United States Patent
Yang et al.

(10) Patent No.: US 12,201,664 B2
(45) Date of Patent: Jan. 21, 2025

(54) **COMPOSITION FOR PREVENTING OR TREATING ALLERGIC DISEASES CONTAINING MIXED EXTRACT OF TWO OR MORE AMONG *ASIASARUM* ROOT, *PLATYCODON* ROOT, AND *CINNAMOMI RAMULUS* AS ACTIVE INGREDIENTS**

(71) Applicants: KOREA INSTITUTE OF SCIENCE AND TECHNOLOGY, Seoul (KR); SEOUL NATIONAL UNIVERSITY R&DB FOUNDATION, Seoul (KR); UNIVERSITY-INDUSTRY COOPERATION GROUP OF KYUNG HEE UNIVERSITY, Yongin-si (KR); KOREA ADVANCED INSTITUTE OF SCIENCE AND TECHNOLOGY, Daejeon (KR)

(72) Inventors: Hyun Ok Yang, Gangneung-si (KR); Keon Wook Kang, Seoul (KR); Sung Won Kwon, Suwon-si (KR); Jeong Hill Park, Seoul (KR); Hocheol Kim, Seoul (KR); Myung Sook Oh, Seoul (KR); Dae Sik Jang, Seoul (KR); Doheon Lee, Daejeon (KR); Hak Cheol Kwon, Gangneung-si (KR); Byung Hwa Jung, Seoul (KR)

(73) Assignees: KOREA INSTITUTE OF SCIENCE AND TECHNOLOGY, Seoul (KR); SEOUL NATIONAL UNIVERSITY R & DB FOUNDATION, Seoul (KR); UNIVERSITY-INDUSTRY COOPERATION GROUP OF KYUNG HEE UNIVERSITY, Gyeonggi-Do (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 635 days.

(21) Appl. No.: 17/059,595

(22) PCT Filed: May 28, 2019

(86) PCT No.: PCT/KR2019/006382
§ 371 (c)(1),
(2) Date: Jun. 10, 2021

(87) PCT Pub. No.: WO2019/231211
PCT Pub. Date: Dec. 5, 2019

(65) Prior Publication Data
US 2021/0338759 A1     Nov. 4, 2021

(30) Foreign Application Priority Data

May 28, 2018   (KR) .................. 10-2018-0060665

(51) Int. Cl.
| | | |
|---|---|---|
| A61K 36/54 | (2006.01) | |
| A61K 36/268 | (2006.01) | |
| A61K 36/346 | (2006.01) | |
| A23K 10/30 | (2016.01) | |
| A23L 33/105 | (2016.01) | |

(52) U.S. Cl.
CPC ............ *A61K 36/54* (2013.01); *A61K 36/268* (2013.01); *A61K 36/346* (2013.01); *A23K 10/30* (2016.05); *A23L 33/105* (2016.08); *A61K 2236/333* (2013.01)

(58) Field of Classification Search
None
See application file for complete search history.

(56) References Cited

FOREIGN PATENT DOCUMENTS

| | | | |
|---|---|---|---|
| JP | 2000-169383 | A | 6/2000 |
| KR | 10-2001-0067653 | A | 7/2001 |
| KR | 10-2001-0068273 | A | 7/2001 |
| KR | 1020030007243 | A | 1/2003 |
| KR | 10-2004-0030371 | A | 4/2004 |
| KR | 10-2018-0055038 | A | 5/2018 |

OTHER PUBLICATIONS

English translation of Kim (KR 20020089275 A)—2002.*
Eunjung Ko et al., "Traditional Korean medicine (SCRT) modulate Th1/Th2 specific cytokine production in mice CD4+ T cell," Journal of Ethnopharmacology, 2004, pp. 121-128, vol. 92, Elsevier Ireland Ltd.
Williams et al., "Cytokine Pathways in Allergic Disease," Toxicologic Pathology, 2012, pp. 205-215, vol. 40, No. 2.
International Search Report mailed Aug. 28, 2019 for PCT/KR2019/006382.
Hee-Yeon Yang et al., "The Effects of Gudambopae-Tang on Changes of Cytokines in Allergic Rhinitis Model," The Journal of Korean Medicine Ophthalmology and Otolaryngology and Dermatology, Aug. 2005, pp. 28-35, vol. 18, English abstract.
Korean Notice of Allowance for KR Application No. 10-2019-0062802 mailed on Feb. 26, 2021.

* cited by examiner

*Primary Examiner* — Susan Hoffman
(74) *Attorney, Agent, or Firm* — CANTOR COLBURN LLP

(57) ABSTRACT

The present invention relates to a pharmaceutical composition for prevention or treatment of an allergic disease comprising a mixed extract of two or more selected from the group consisting of *Asiasarum* root, *Platycodon* root, and *Cinnamomi ramulus* as an active ingredient; a method for prevention or treatment of an allergic disease using the pharmaceutical composition; and a health functional food and a feed composition for improvement of an allergic disease. The composition and method of the invention can specifically inhibit the differentiation of Th2 cells and thus can be effectively used as a composition for prevention or treatment of an allergic disease.

6 Claims, 17 Drawing Sheets

1st (n=4/group)

2nd (n=4/group)

significant difference from the control group at p<0.01
significant difference from the control group at p<0.001
* significant difference from the AD group at p<0.05
** significant difference from the AD group at p<0.01
*** significant difference from the AD group at p<0.001

COMPOSITION FOR PREVENTING OR TREATING ALLERGIC DISEASES CONTAINING MIXED EXTRACT OF TWO OR MORE AMONG *ASIASARUM* ROOT, *PLATYCODON* ROOT, AND *CINNAMOMI RAMULUS* AS ACTIVE INGREDIENTS

TECHNICAL FIELD

The present invention relates to a pharmaceutical composition for prevention or treatment of an allergic disease, the composition comprising a mixed extract of two or more selected from the group consisting of *Asiasarum* root, *Platycodon* root, and *Cinnamomi ramulus* as an active ingredient; a method for prevention or treatment of an allergic disease using the pharmaceutical composition; and a health functional food and a feed composition for improvement of an allergic disease.

BACKGROUND ART

An allergic disease refers to a disease which occurs due to an allergy. An allergy is an antigen-antibody reaction which occurs when a certain kind of substance (i.e., an antigen or allergen (an allergy-causing factor)), that had previously entered the body of an individual and caused production of an antibody against it, re-enters the body of the same individual as the same antigen (Dictionary of Nutrition, Mar. 15, 1998, CHAE Bum-Seok and KIM Eul-Sang). The main allergic diseases include respiratory diseases, dermatitis (including atopic dermatitis), drug eruptions, drug allergies, serum diseases, etc., and these diseases show various types depending on the type of allergens and tissues causing allergic reactions. For diagnosis of an allergic disease, the progression and the time of onset of the disease of the patient or his/her family members, living environments, contents of diets, etc. up to the time point of diagnosis can be considered.

An allergic respiratory disease means a respiratory disease among the diseases in which an allergic reaction is involved. Representative allergic respiratory diseases include bronchial asthma, bronchitis, and allergic rhinitis. Bronchial asthma is a medical condition in which the bronchi in the lungs become very sensitive, sometimes narrowing the bronchi and thereby causing shortness of breath and severe coughing. It is an allergic disease caused by an allergic inflammatory reaction of the bronchi. Due to recent westernization and changes in dietary habits, the prevalence of bronchial asthma is in an increasing trend, and accordingly, the relevant medical treatment and the costs involved therein are also increasing.

According to a report by Grand View Research, which is a market research/consulting organization, it is estimated that about 300 million people have bronchial asthma worldwide, and it is a disease of global interest in public health with a prevalence of 4.83%. According to the Ministry of Health and Welfare of Korea in 2012, the prevalence of bronchial asthma in Korean people aged 19 or older as of 2010 was 3.1%, due to a continued increase from 1.4% in 2001. In addition, the prevalence of bronchial asthma among elementary school students in 2010 was 10.2%, which was the highest among the age groups, and the prevalence of bronchial asthma in Korean people aged 70 or older was 6.7%, becoming the cause of some of deaths along with a chronic obstructive pulmonary disease. In Korea, while the total annual social cost incurred due to bronchial asthma in 2004 was very costly to be about 4 trillion in Korean Currency (Won), the environment established for the treatment of bronchial asthma was extremely poor. Therefore, there is an urgent need for an effective management of a bronchial asthma disease.

Bronchitis is inflammation of the bronchi in the lungs. Unlike acute bronchitis where more than 90% of the causes are viral infections, chronic bronchitis caused by air pollution or chronic inhalation of highly irritating dust in the occupational field (e.g., coal mining, grain processing, textile manufacturing, animal husbandry, metal casting, etc.) shows wheezing, shortness of breath, and low oxygen saturation during exercise, and generation of sputum and coughing are continued for more than 2 years, and last more than 3 months every year. People who are aged 45 or older, smokers, living in areas with high air pollution, and those with asthma are known to have a higher risk of developing chronic bronchitis.

Allergic rhinitis is a disease which occurs such that when the nasal mucosa is hypersensitive to certain substances, after exposure of the substance causing allergies (i.e., allergens or antigens) to the nasal mucosa, inflammatory cells mediated by various types of immunoglobulin E (IgE) antibodies, including mast cells and eosinophils, flock to the stimulation site, and thereby inflammatory reactions occur by various mediators secreted by them. Allergic rhinitis is characterized by three main symptoms of successive paroxysmal sneezing, clear runny nose, and stuffy nose, and anyone having two or more of these symptoms may be suspected of having allergic rhinitis. In addition to these characteristic symptoms, allergic rhinitis may be accompanied by itching around the nose, headache, deterioration in olfactory functions, etc. and may be accompanied by complications such as otitis media, sinusitis, pharyngitis, etc.

Atopic dermatitis (AD) is a chronic relapsing eczema disease that begins from infancy and is accompanied by itching. It is known to be caused by cells involved in the immune response, such as macrophages, granulocytes (e.g., basophils, eosinophils, neutrophils, and mast cells), Th2 cells, etc. (Sicherer S H et al., 1999), and it is a complex disease resulting from an increase in blood IgE against foreign antigens (Rousset F et al., 1991; Kleij H P et al., 2004).

AD is a disease which worsens the quality and values of lives for patients and those around them, and the incidence rate of AD patients is increasing worldwide. Although steroids, antihistamines, etc. are used as therapeutic agents for AD, it is difficult to expect the cure by these drugs, and rather, the use of these drugs is very limited due to their side effects during a long-term use.

Such allergic diseases occur by an interaction between genetic and environmental factors, and in most cases, they are typical intractable chronic diseases that are not easy to cure. Host factors include genetic factors, obesity, sex, etc. and environmental factors include dust mites, pollen, pets, respiratory infectious viruses, exercise, drugs (e.g., aspirin, etc.), smoking, air pollution, chemicals, foods, and stress. It may be possible to find the causes of these allergic diseases by methods such as a skin prick test for allergy, an allergy-specific antibody test, an allergen bronchial asthma provoking test, etc., but it is difficult to identify the exact cause.

Among these allergic diseases, bronchial asthma increases the immune response of the T helper type 2 (Th2) type during various mechanisms of pathogeneses, thereby increasing the secretion of interleukin-4, 5, 13, etc. (Liu et al., 2006; Williams et al., 2012), and in conjunction with this response, many inflammatory cells, including eosinophils, migrate and infiltrate into lung tissue (Zhou et al., 2011).

Additionally, inflammatory cells also release various proinflammatory and chemotactic factors, exacerbating the inflammatory response, thereby increasing mucus secretion of goblet cells in the tracheas, and causing trachea hyper-responsiveness (Chibana et al., 2008). Due to this series of reactions, bronchial asthma patients have clinical symptoms such as dyspnea, cyanosis, chest pain, etc. Atopic dermatitis is also known as a Th2-mediated immune disease.

Currently, drugs used for the treatment of allergic diseases include steroid preparations, antihistamines, bronchodilators, antibiotics, etc. Steroid preparations and antibiotics are used for the treatment of allergic diseases through suppression of immune and inflammatory reactions, and bronchodilators are used for offsetting clinical symptoms (e.g. dyspnea, etc.) at the onset of clinical symptoms. However, these drugs are very limited in their use as antibiotics due to side effects, such as resistance to antibiotics, immunosuppression, and myelosuppression, and other side effects during a long-term use. Therefore, there is a need for the development of a natural compound or novel compound which can overcome these side effects and which has low toxicity and excellent therapeutic effects.

DISCLOSURE

Technical Problem

The present inventors have made extensive studies to develop a natural material having an excellent therapeutic effect on allergic diseases. As a result, they have discovered that an *Asiasarum* root extract, a *Platycodon* root extract, or a *Cinnamomi ramulus* extract has an excellent effect on allergic diseases, and in addition, when two or more extracts among the *Asiasarum* root, *Platycodon* root, and *Cinnamomi ramulus* extracts were mixed, the mixed extract showed a more excellent effect on the treatment of allergic diseases, thereby completing the present invention.

Technical Solution

An object of the present invention is to provide a pharmaceutical composition for prevention or treatment of an allergic disease, the composition including a mixed extract of two or more selected from the group consisting of *Asiasarum* root, *Platycodon* root, and *Cinnamomi ramulus* as an active ingredient.

Another object of the present invention is to provide a method of prevention or treatment of an allergic disease, which includes administering a mixed extract of two or more selected from the group consisting of *Asiasarum* root, *Platycodon* root, and *Cinnamomi ramulus* to a subject.

Still another object of the present invention is to provide a health functional food for prevention or improvement of an allergic disease, the composition including a mixed extract of two or more selected from the group consisting of *Asiasarum* root, *Platycodon* root, and *Cinnamomi ramulus* as an active ingredient.

Still another object of the present invention is to provide a feed composition for prevention or improvement of an allergic disease, the composition comprising a mixed extract of two or more selected from the group consisting of *Asiasarum* root, *Platycodon* root, and *Cinnamomi ramulus* as an active ingredient.

Advantageous Effects

The composition of the present invention, which contains a mixed extract of two or more selected from the group consisting of *Asiasarum* root, *Platycodon* root, and *Cinnamomi ramulus* as an active ingredient, can specifically inhibit the differentiation of Th2 cells and thus can be effectively used as a composition for prevention or treatment of an allergic disease.

BEST MODE FOR CARRYING OUT THE INVENTION

Figure 1:
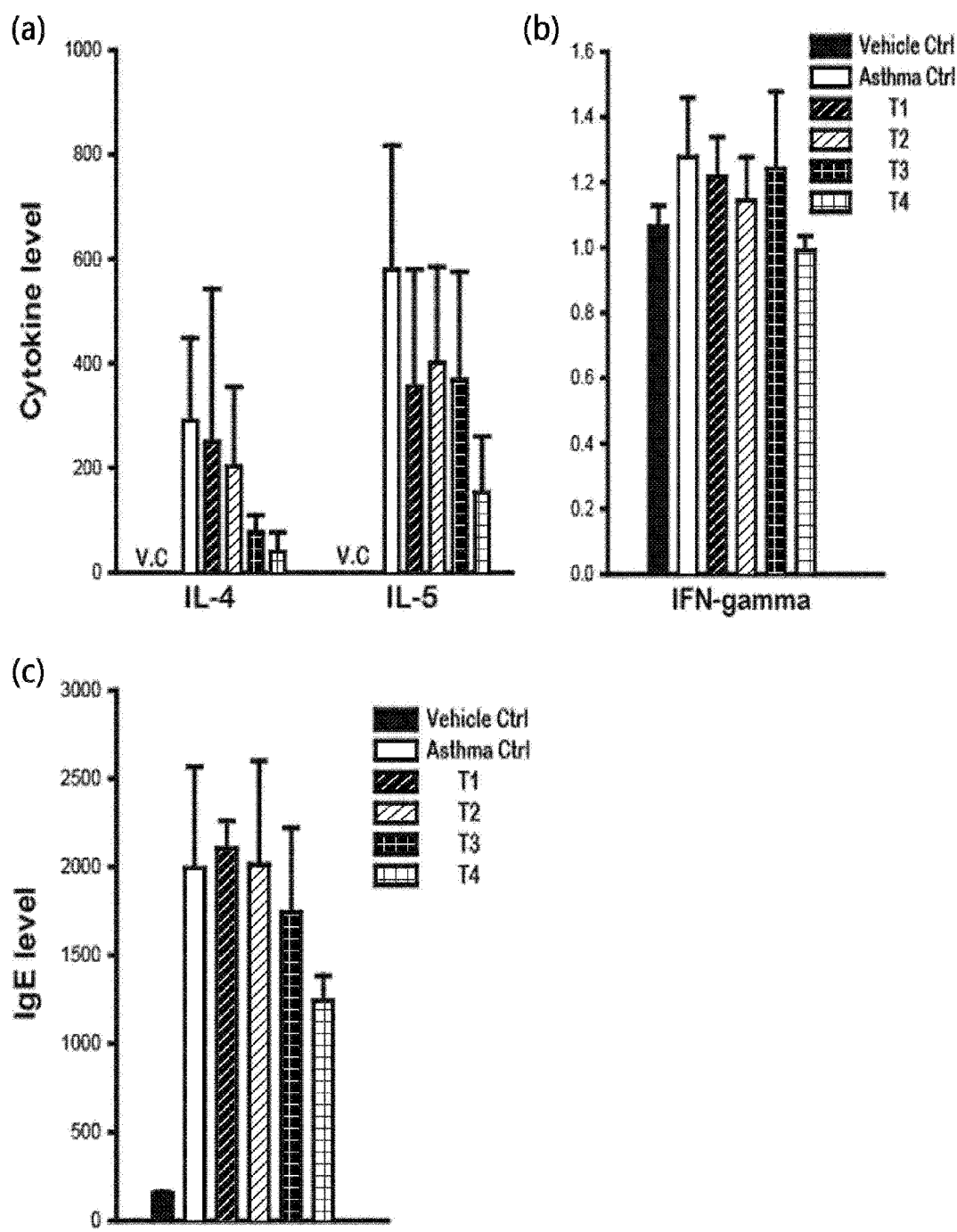
FIG. 1 shows graphs illustrating the analysis results of a leachate from the bronchus and serum IgE according to trachea exposure of BS012.

The present invention is described in detail as follows. Meanwhile, respective descriptions and embodiments disclosed in the present invention may also be applied to other descriptions and embodiments. That is, all combinations of various elements disclosed in the present invention fall within the scope of the present invention. Further, the scope of the present invention is not limited by the specific description below.

To achieve the above objects, one aspect of the present invention provides a pharmaceutical composition for prevention or treatment of an allergic disease, which contains a mixed extract of two or more selected from the group consisting of *Asiasarum* root, *Platycodon* root, and *Cinnamomi ramulus* as an active ingredient.

As used herein, the term "*Asiasarum* root" is an herbal material, which is prepared by drying the roots of *Asiasarum heterotropoides* and *Asiasarum sieboldi* (i.e., perennial plants belonging to the family Aristolochiaceae) and is also called roots of *Asiasarum sieboldi*. *Asiasarum heterotropoides* grows in the shade of wetlands of a deep mountain in various places, and *Asiasarum sieboldi* is widely distributed in the mountains south of the central part of South Korea. *Asiasarum* root has a spicy taste and a mild medicinal property. It has efficacies for use in the treatment of a headache, a stuffy nose, a fever, phlegm, coughing, dyspnea, etc. caused by colds and cold-wind. In pharmacological experiments, it was found that *Asiasarum* root has antipyretic, local anesthesia, antibacterial effects, etc.

As used herein, the term "*Platycodon* root" is an herbal material, which is prepared by removing the roots or periderm of *Platycodon grandiflorum* that belongs to the family Campanulaceae. *Platycodon* root acts on the lungs and thereby treats symptoms such as frequent coughing, much phlegm, and uncomfortable breathing, and it also clears the lungs, relieves stuffy chest, and relieves cold atmosphere in the stomach to stop coughing and remove phlegm. It is also used to treat systemic edema caused by a difficulty in urination along with production of a low amount of urine, and to treat sore throat, cough, phlegm, stuffy nose, bronchial asthma, bronchitis, pleurisy, headache, chills, tonsillitis, etc. caused by a cold. As pharmacological actions of *Platycodon* root, an expectorant action, a hypoglycemic action, a cholesterol lowering action, and an inhibitory action of scabies have been reported.

As used herein, the term "*Cinnamomi ramulus*" is an herbal material, which is prepared using young branches of *Cinnamomum cassia* Blume or other taxonomically related plants of the same species. It induces sweating by opening skin pores in the early stage of a cold; relieves the pain in the shoulder, back, etc., and the pain in the limb joints; promotes the energy-blood circulation and treats lack of stamina. As pharmacological actions of *Cinnamomi ramulus*, a sweating action, an antipyretic action, an analgesic action, a cardiac strengthening action, an antiviral action, an antibacterial action, etc. have been reported.

As used herein, the term "extract" may refer to a resulting product such as components in a liquid state, which is obtained by immersing a target material in various solvents followed by extraction at room temperature or in a heated state for a certain period of time; a resulting product such as solid contents, which is obtained by removing the solvents from the components in a liquid state; etc. Moreover, the term "extract" may be comprehensively interpreted as including all of the diluents, the resulting products, concentrates thereof, crude purified products thereof, purified products, etc.

As used herein, the term "mixed extract" may be one which is used for the purpose of improving the effect by mixing these extracts.

The mixed extract may be a mixed extract in which three of *Asiasarum* root, *Platycodon* root, and *Cinnamomi ramulus* are mixed; or a mixture in which two selected from the group consisting of *Asiasarum* root, *Platycodon* root, and *Cinnamomi ramulus* are mixed.

The mixed extract may be one which is prepared by mixing the extracts obtained from each material, or may be one which is prepared by mixing at the level of raw materials followed by extraction of the materials as a whole, but the mixed extract is not limited thereto.

The mixed extract of three of *Asiasarum* root, *Platycodon* root, and *Cinnamomi ramulus* may be one, in which *Asiasarum* root, *Platycodon* root, and *Cinnamomi ramulus* are mixed at a mixing ratio of (0.1 to 2):(0.1 to 4):(0.1 to 4), specifically (0.5 to 1.5):(0.5 to 3):(0.5 to 3), more specifically (0.7 to 1.5):(0.7 to 2.5):(0.7 to 2.5). In the case of a mixed extract of two, the mixed extract may be one in which *Asiasarum* root and *Platycodon* root are mixed at a mixing ratio of (0.1 to 2):(0.1 to 4), one in which *Asiasarum* root and *Cinnamomi ramulus* are mixed at a mixing ratio of (0.1 to 2):(0.1 to 4), or one in which *Platycodon* root and *Cinnamomi ramulus* are mixed at a mixing ratio of (0.1 to 4):(0.1 to 4), specifically one in which *Asiasarum* root and *Platycodon* root are mixed at a mixing ratio of (0.5 to 1.5):(0.5 to 3), one in which *Asiasarum* root and *Cinnamomi ramulus* are mixed at a mixing ratio of (0.5 to 1.5):(0.5 to 3), or one in which *Platycodon* root and *Cinnamomi ramulus* are mixed at a mixing ratio of (0.5 to 3):(0.5 to 3), and more specifically one in which *Asiasarum* root and *Platycodon* root are mixed at a mixing ratio of (0.7 to 1.5):(0.7 to 2.5), one in which *Asiasarum* root and *Cinnamomi ramulus* are mixed at a mixing ratio of (0.7 to 1.5):(0.7 to 2.5), or one in which *Platycodon* root and *Cinnamomi ramulus* are mixed at a mixing ratio of (0.7 to 2.5):(0.7 to 2.5), but the mixing ratio is not limited thereto.

The mixed extract of two or more selected from the group consisting of *Asiasarum* root, *Platycodon* root, and *Cinnamomi ramulus* refers to not only crude extracts of *Asiasarum* root, *Platycodon* root, and *Cinnamomi ramulus*, but also all of forms thereof by further processing of these extracts.

The solvent to be used for the extraction may be selected from the group consisting of water, alcohol, and a mixture thereof, specifically selected from C1 to C4 low grade alcohol or a mixed solvent thereof, more specifically methanol or ethanol, and even more specifically ethanol, but the solvent to be used is not limited thereto. The amount of the extraction solvent may be 2- to 10-fold the dry weight of the plant, but is not limited thereto.

As the extraction method, hot water extraction, immersion extraction, reflux cooling extraction, ultrasonic extraction, etc. may be used. The temperature at the time of extraction may be specifically 10° C. to 100° C., and more specifically room temperature, but the extraction temperature is not limited thereto. The extraction time may be specifically 30 minutes to one day, more specifically 1 hour to 20 hours, but the extraction time is not limited thereto.

In the present specification, the mixed extract of *Asiasarum* root, *Platycodon* root, and *Cinnamomi ramulus* may be used interchangeably with BS012.

As used herein, the term "allergic disease" refers to a disease refers to a disease which occurs due to an allergy. An allergy is an antigen-antibody reaction which occurs when a certain kind of substance (i.e., an antigen or allergen (an allergy-causing factor)), that had previously entered the body of an individual and caused production of an antibody against it, re-enters the body of the same individual as the same antigen. Specifically, the allergic disease may be an allergic respiratory disease or atopic dermatitis, but the allergic disease is not limited thereto.

As used herein, the term "allergic respiratory disease" refers to a respiratory disease among the diseases involving an allergic reaction, and a representative allergic respiratory disease may include bronchial asthma, bronchitis, and allergic rhinitis.

As used herein, the term "bronchial asthma" refers to a disease in which the bronchi in the lungs are in a very sensitive state and are sometimes narrowed, causing severe coughing along with symptoms of shortness and a wheezing sound of breath. It is one of the inflammatory diseases caused by an allergic inflammatory reaction of the bronchi.

As used herein, the term "bronchitis" refers to inflammation that occurs in the bronchi of the lungs. Unlike acute bronchitis, which is caused by viral infections in more than 90% of the cases, chronic bronchitis, where air pollution or chronic inhalation of highly irritating dust in occupations (e.g., coal mining, processing of grain, manufacture of textiles, livestock production, metal casting, etc.) serves as the cause, exhibits wheezing, shortness of breath, and a low degree of oxygen saturation during exercise, and phlegm and cough are persistent for more than two years and last for more than three months each year.

As used herein, the term "allergic rhinitis" is a disease which occurs such that when the nasal mucosa is hypersensitive to certain substances, after exposure of the substance causing allergies (i.e., allergens or antigens) to the nasal mucosa, inflammatory cells mediated by various types of immunoglobulin E (IgE) antibodies, including mast cells and eosinophils, flock to the stimulation site, and thereby inflammatory reactions occur by various mediators secreted by them. Allergic rhinitis is characterized by having three major symptoms of successive paroxysmal sneezing, clear nasal discharge, and stuffy nose, and allergic rhinitis can be suspected when two or more of these three symptoms are present. In addition to the characteristic symptoms, symptoms such as itching around the nose, headache, loss of smell, etc. may be accompanied, and complications such as otitis media, sinusitis, and sore throat may be accompanied.

As used herein, the term "atopic dermatitis (AD)" refers to a chronic relapsing eczema disease accompanied by itching, whose onset starts from infancy. Atopic dermatitis is known to be caused by cells involved in the immune response, such as macrophages; basophils, eosinophils, neutrophils, and mast cells, which are called granulocytes; and Th2 cells, and it is a complex disease manifested by an increase in blood IgE to foreign antigens.

The allergic disease is a representative intractable chronic disease caused by an interaction between a genetic factor and an environmental factor, and it is not easy to cure in most cases. Host factors include genetic factors, obesity, gender, etc., and environmental factors include dust mites, pollen, pets, respiratory infection viruses, exercises, drugs (e.g., aspirin), smoking, air pollution, chemicals, food, and stress.

Among them, in the case of bronchial asthma, a Th2 type of immune response is promoted among various pathogenic mechanisms, and as a result, the secretion of interleukin-4, 5, 13, etc. is increased. In connection with this reaction, many inflammatory cells, including eosinophils, migrate and infiltrate into the lung tissue. In addition, these inflammatory cells release various pro-inflammatory factors and chemotactic factors, further exacerbating the inflammatory response, increasing mucus secretion of goblet cells in the trachea, and causing irritability of the trachea. Due to this series of reactions, patients with bronchial asthma develop clinical symptoms such as dyspnea, cyanosis, chest pain, etc. Atopic dermatitis is also known as a Th2-mediated immune disease.

The composition of the present invention may be for the treatment of an allergic disease through the inhibition of Th2 cell differentiation.

Figure 4:
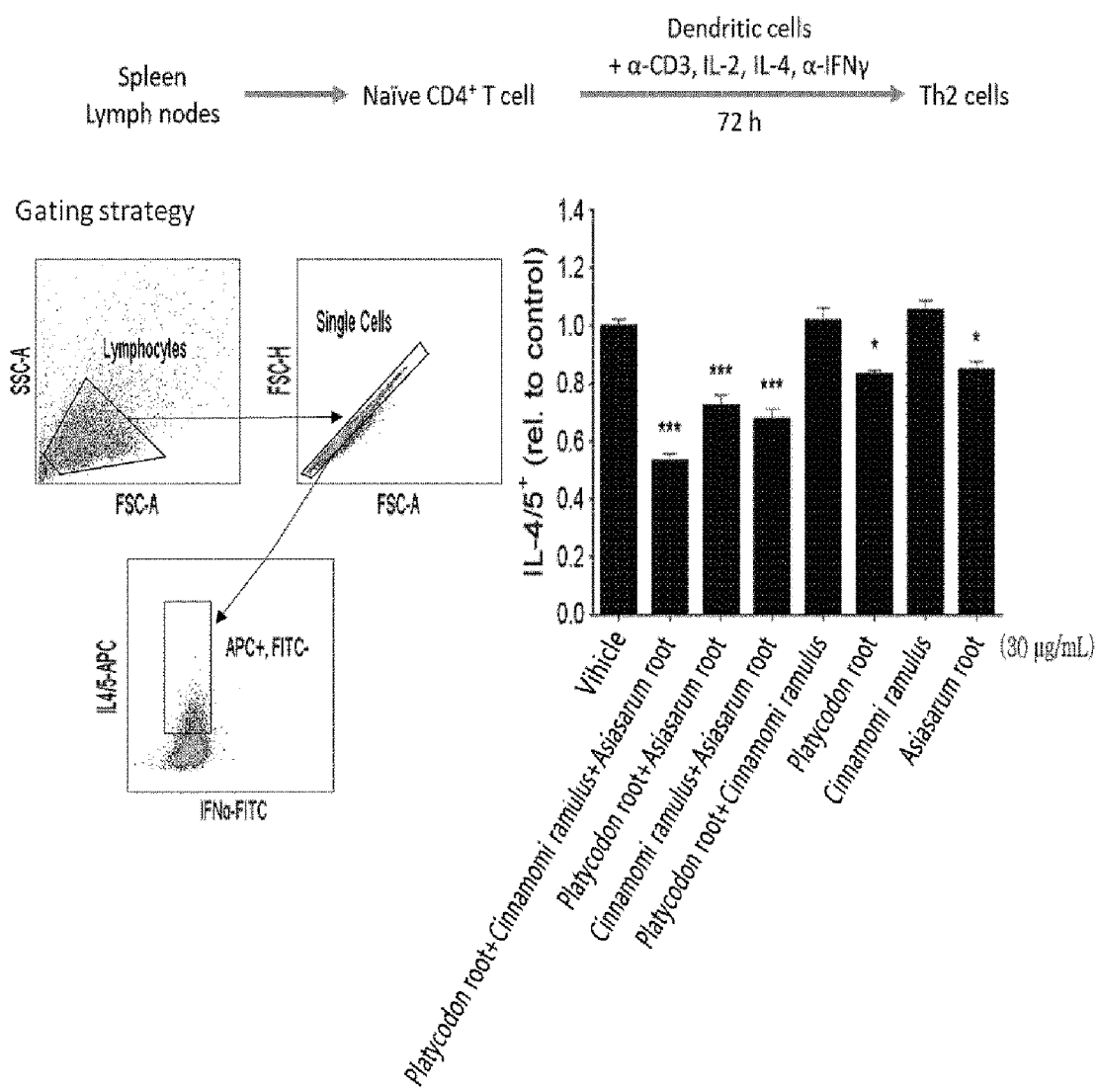
FIG. 4 shows the analysis results of differentiation conditions of Th2 and the differentiation level of Th2 according to the treatment with an extract of each of *Asiasarum* root, *Platycodon* root, and *Cinnamomi ramulus*, and a mixture thereof.

In a specific embodiment of the present invention, when T cells were treated with BS012 while culturing them under conditions where T cells cannot be differentiated into Th2 cells, a remarkable inhibitory effect against Th2 differentiation was shown compared to the control group (FIG. 4).

In addition, the composition of the present invention may be one for treating an allergic disease through the inhibition of Th2-specific differentiation.

Figure 3:
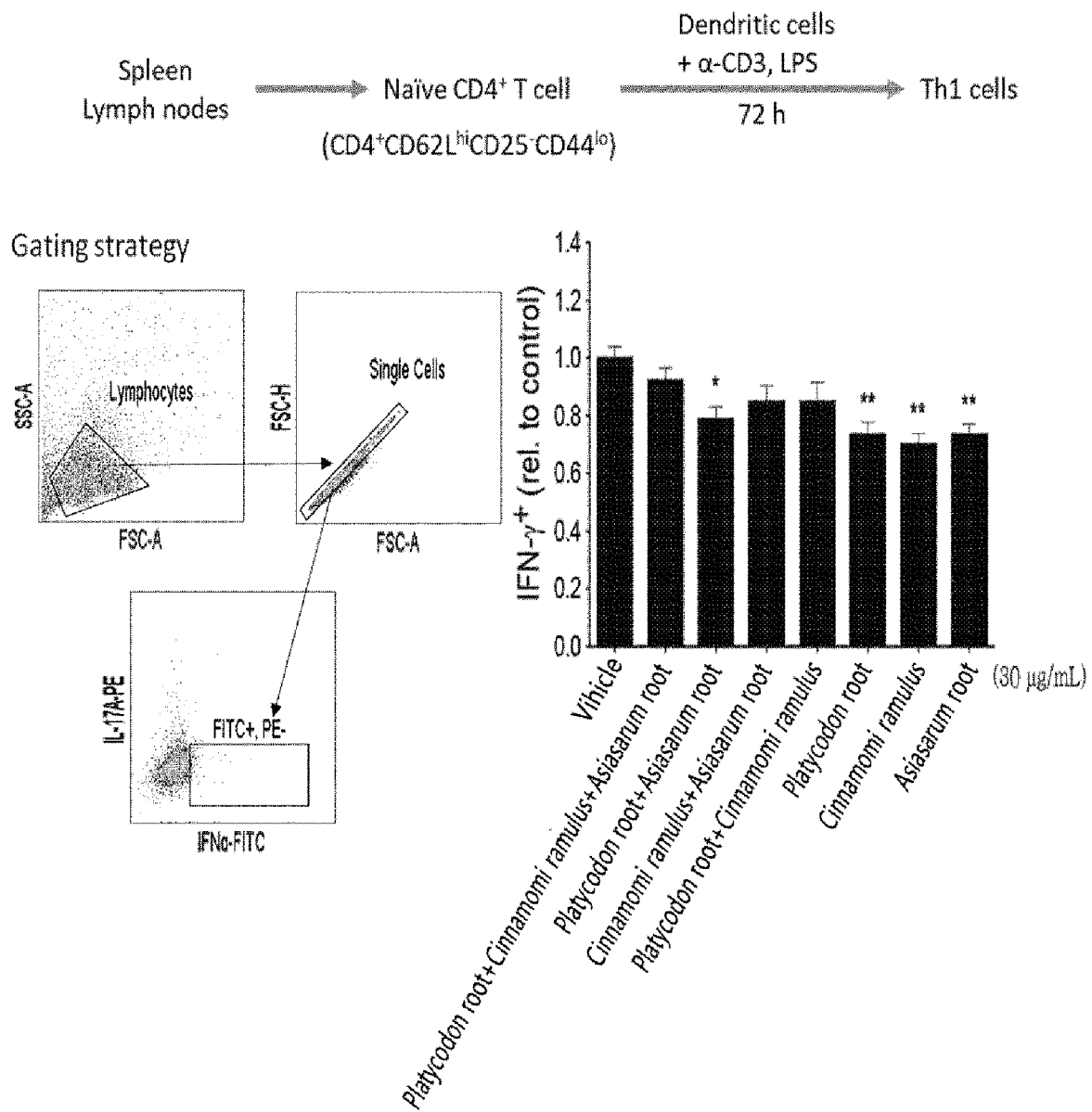
FIG. 3 shows the analysis results of differentiation conditions of Th1 and the differentiation level of Th1 according to the treatment with an extract of each of *Asiasarum* root, *Platycodon* root, and *Cinnamomi ramulus*, and a mixture thereof.
Figure 5:
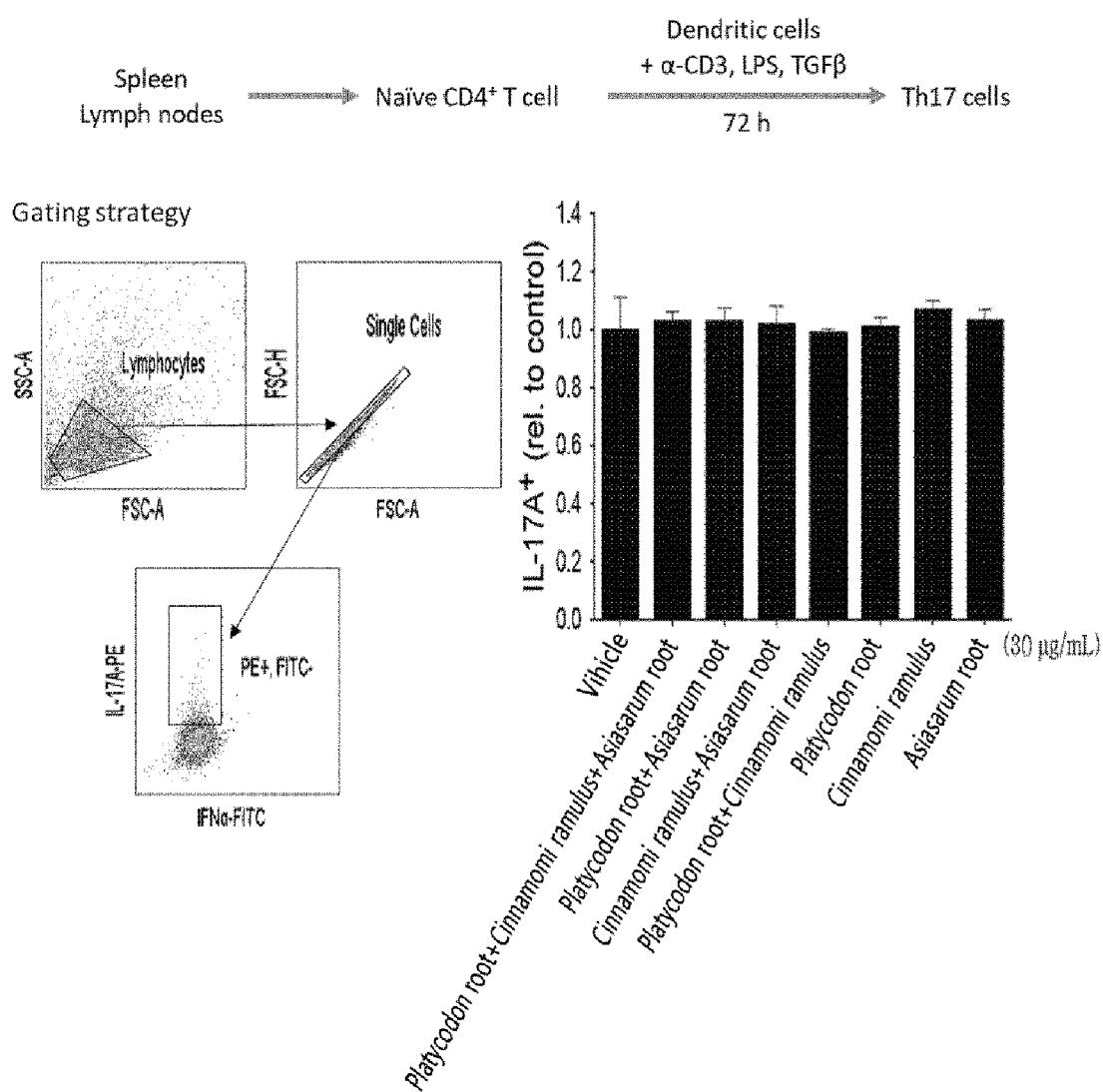
FIG. 5 shows the analysis results of differentiation conditions of Th17 and the differentiation level of Th17 according to the treatment with an extract of each of *Asiasarum* root, *Platycodon* root, and *Cinnamomi ramulus*, and a mixture thereof.

In a specific embodiment of the present invention, when T cells were treated with BS012 while culturing them under conditions where T cells can be differentiated into Th1, Th2, and Th17 cells, respectively, there was remarkable inhibition against the differentiation into Th2 cells; however, the inhibitory effect against the differentiation into Th1 cells or Th17 cells was either negligible or absent (FIGS. 3 to 5).

Figure 14:
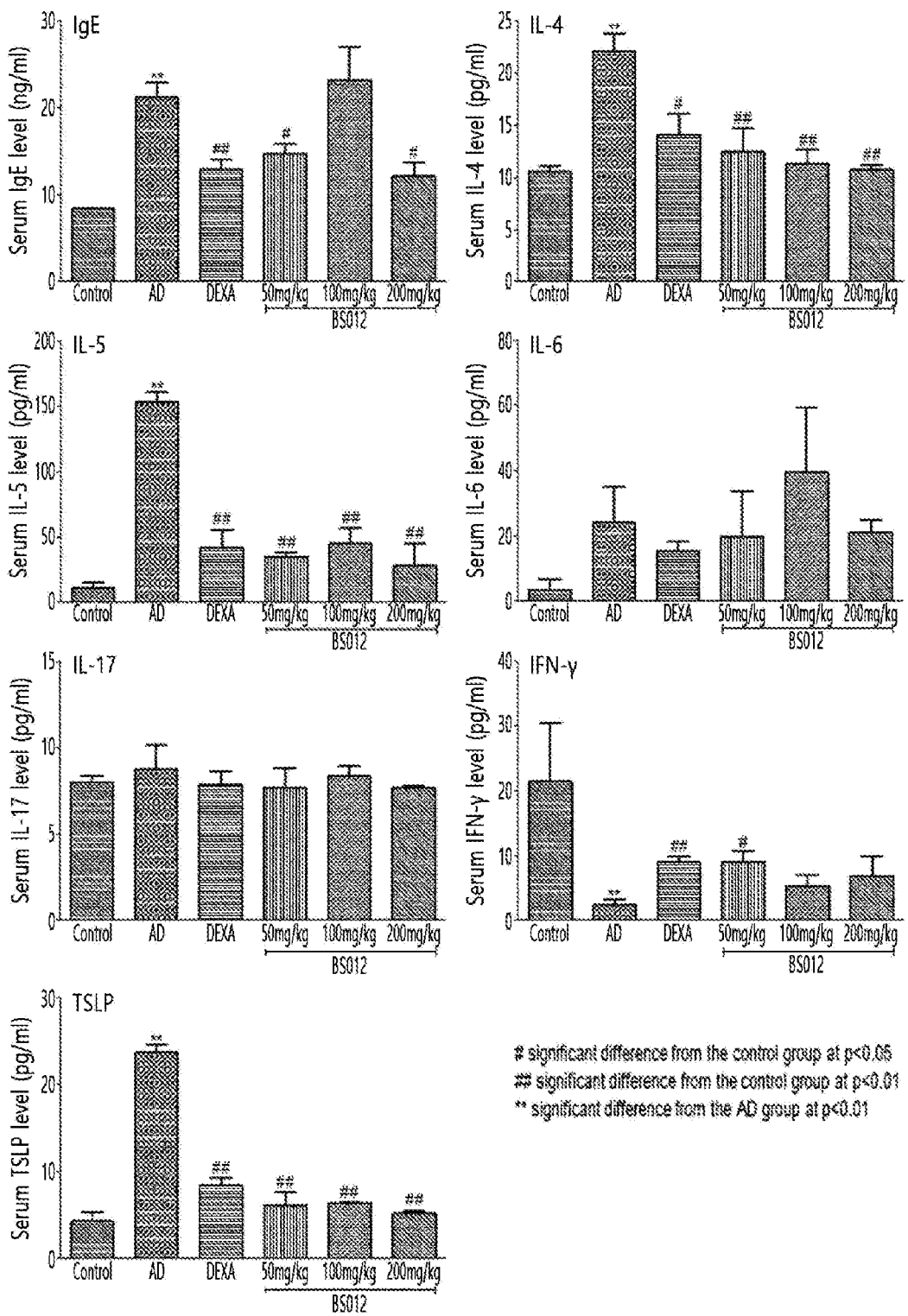
FIG. 14 shows graphs illustrating the analysis results of serum IgE and cytokines relating to atopic dermatitis with an extract of each of *Asiasarum* root, *Platycodon* mot, and *Cinnamomi ramulus*, and a mixture thereof.

In addition, in a specific embodiment of the present invention, when the mixed extract according to the present invention was orally administered through a tube and the Th2-associated cytokines were analyzed, it was confirmed that BS012 inhibited Th2-associated cytokines (FIG. 14).

From this result, it can be determined that BS012 exhibits a Th2-specific differentiation inhibitory effect.

While Th1 cells are known to be mainly associated with cell-mediated immunity and autoimmune diseases and Th17 cells are known to be associated with autoimmune diseases and inflammatory reactions (e.g., rheumatoid arthritis), Th2 cells are known to be mainly associated with allergic reactions, in particular an allergic disease, specifically an allergic respiratory disease and atopic dermatitis. Therefore, it can be determined that BS012 provided in the present invention can treat an allergic disease, and specifically an allergic respiratory disease and atopic dermatitis, through the inhibition of Th2 cell differentiation.

As used herein, the term "prevention" may refer to any action that inhibits or delays the onset of an allergic disease by administering the mixed extract according to the present invention to an individual.

As used herein, the term "treatment" may refer to any action that improves or beneficially alters the symptoms of an allergic disease by administering the composition of the present invention to an individual suspected of having a developed allergic disease.

As used herein, the term "pharmaceutical composition" may refer to one which is prepared for the purpose of preventing or treating diseases, and can be formulated for use in various forms according to each conventional method. For example, the pharmaceutical composition may be formulated into a dosage form (e.g., powders, granules, tablets, capsules, suspensions, emulsions, syrups, etc.) and may be formulated and used in the form of preparations for external use, suppositories, and sterile injectable solutions. Specifically, the pharmaceutical composition may be formulated for use in a form suitable for eye drop administration (e.g., eye drop preparations, cream preparations, ointment preparations, gel preparations, or lotion preparations).

The pharmaceutical composition of the present invention may be prepared in the form of a pharmaceutical composition for preventing or treating wounds, which further contains an appropriate carrier, excipient, or diluent commonly used in the preparation of pharmaceutical compositions. The carrier may include a non-naturally occurring carrier.

In the present invention, carriers, excipients, and diluents that may be included in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

In the case of formulation, the pharmaceutical composition is prepared using diluents or excipients (e.g., fillers, extenders, binders, wetting agents, disintegrants, and surfactants) that are commonly used. Solid preparations for oral administration include tablets, pills, powders, granules, capsules, etc. These solid preparations are prepared by mixing at least one excipient (e.g., starch, calcium carbonate, sucrose or lactose, gelatin, etc.) with the extract of mulberry leaves and fractions thereof. In addition to simple excipients, lubricants (e.g., magnesium stearate, and talc) are also used. Liquid preparations for oral administration include suspensions, liquid preparations for internal use, emulsions, syrups, etc., and various excipients (e.g., wetting agents, sweetening agents, fragrances, preservatives, etc.) may be used in addition to water and liquid paraffin, which are simple diluents commonly used. Preparations for parenteral administration include sterile aqueous solutions, non-aqueous solutions, suspending agents, emulsions, lyophilized preparations, and suppositories. As the non-aqueous solvents and suspending agents, propylene glycol, polyethylene glycol, vegetable oil (e.g., olive oil), an injectable ester (e.g., ethyl oleate), etc. may be used. As a base for suppositories, witepsol, macrogol, tween 61, cacao butter, laurin butter, glycerogelatin, etc. may be used.

Another aspect of the present invention provides a method for prevention or treatment of an allergic disease, which includes administering a mixed extract of two or more selected from the group consisting of *Asiasarum* root, *Platycodon* root, and *Cinnamomi ramulus* to a subject.

The terms "*Asiasarum* root", "*Platycodon* root", "*Cinnamomi ramulus*", "mixture", "allergic disease", "prevention", and "treatment" are as described above.

As used herein, the term "subject" may refer to all animals, including humans, who have developed or are likely to develop an allergic disease. The animals may be not only humans but also mammals (e.g., cows, horses, sheep, pigs, goats, camels, antelopes, dogs, cats, etc.) who are in need of treatment for symptoms similar to the allergic disease, but the animals are not limited thereto.

The preventive or treatment method of the present invention may specifically include administering the composition in a pharmaceutically effective amount to a subject who has developed or is at risk of developing an allergic disease.

As used herein, the term "administration" refers to introducing the pharmaceutical composition of the present invention to a patient by any suitable method. The administration route of the composition of the present invention may be administered through various routes as long as it can reach the target tissue. According to the desired purpose, the composition may be administered through eye drops, intraperitoneal administration, intravenous administration, intramuscular administration, subcutaneous administration, intradermal administration, transdermal patch administration, oral administration, intranasal administration, intrapulmonary administration, rectal administration, etc., specifically oral administration and intranasal administration, and more specifically intratracheal administration, laryngopharyngeal inhalation exposure, and nasal inhalation exposure. The active ingredients in the pharmaceutical composition may vary depending on the age, sex, weight, pathological conditions and severity of the subject to be administered, administration route, or a prescriber's decision. Decision of the amount to be applied based on these factors is within the level of those skilled in the art. The daily administration dose thereof may be, for example, in the range of 0.1 mg/kg/day to 1,000 mg/kg/day, 0.5 mg/kg/day to 900 mg/kg/day, 1 mg/kg/day to 800 mg/kg/day, 2 mg/kg/day to 700 mg/kg/day, 5 mg/kg/day to 600 mg/kg/day, 10 mg/kg/day to 500 mg/kg/day, 20 mg/kg/day to 400 mg/kg/day, 30 mg/kg/day to 300 mg/kg/day, 40 mg/kg/day to 250 mg/kg/day, and more specifically 50 mg/kg/day to 200 mg/kg/day. The administration frequency of the composition of the present invention is not particularly limited, but the composition may be administered once daily or several times in divided doses. The administration dose does not in any way limit the scope of the present invention.

Figure 2:
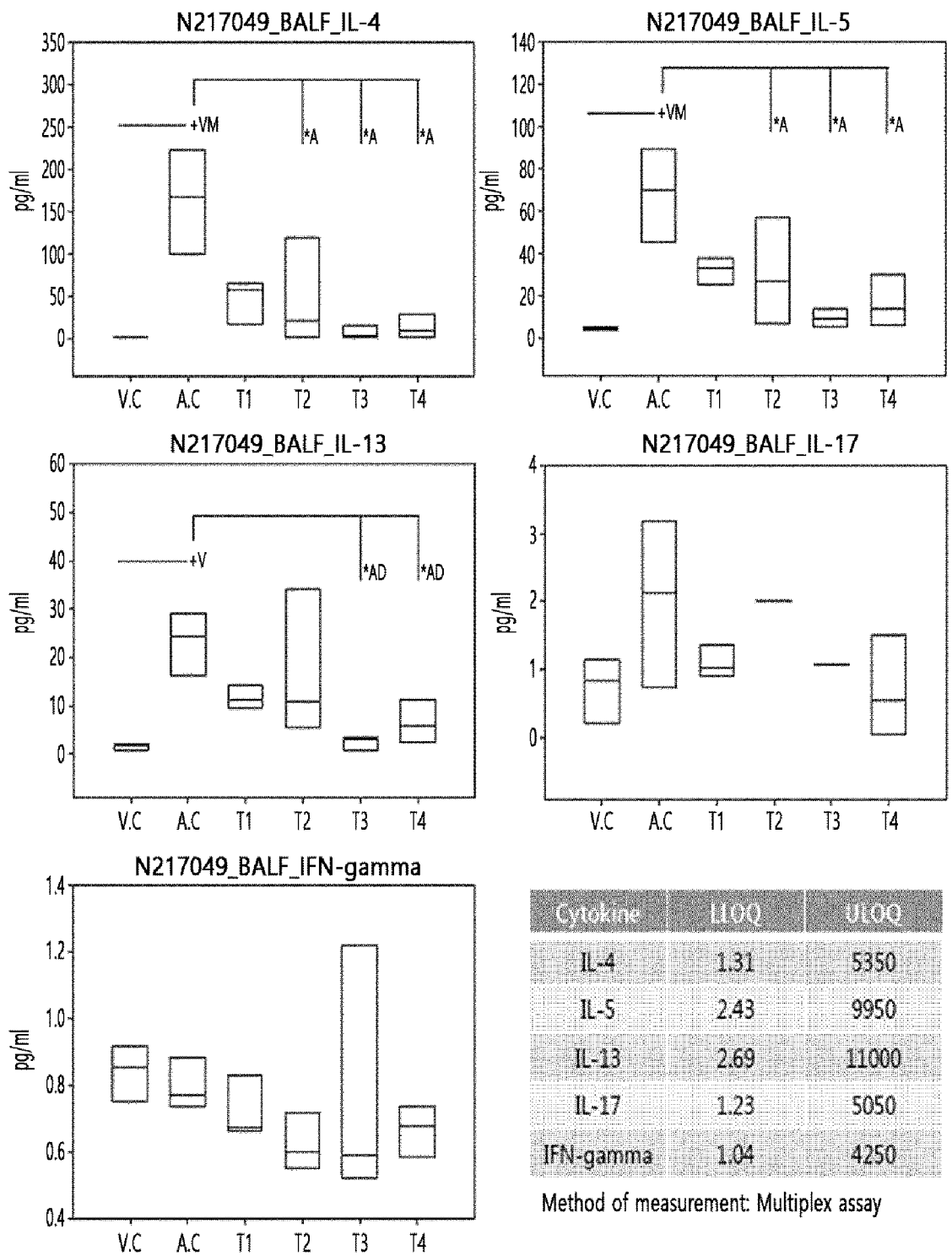
FIG. 2 shows the analysis results of a leachate from the bronchus according to nasal inhalation exposure of BS012.

In a specific embodiment of the present invention, in order to confirm the difference in effect according to the administration route of the mixed extract of the present invention, the extract was administered through intratracheal administration and nasal inhalation exposure, and bronchial leachate and serum IgE were analyzed. As a result, it was confirmed that both administration routes specifically inhibited Th2-associated cytokines, thus confirming that BS012 has an effect of treating an allergic respiratory disease in both administration routes (FIGS. 1 and 2).

Additionally, in a specific embodiment of the present invention, the mixed extract according to the present invention was orally administered through a tube, and serum IgE and Th2-associated cytokines were analyzed. As a result, it was confirmed that BS012 inhibited serum IgE and Th2-associated cytokines thus having an effect of treating atopic dermatitis (FIG. 14).

Still another aspect of the present invention provides a health functional food for prevention or improvement of an allergic disease, which contains a mixed extract of two or more selected from the group consisting of *Asiasarum* root, *Platycodon* root, and *Cinnamomi ramulus* as an active ingredient.

The terms "*Asiasarum* root", "*Platycodon* root", "*Cinnamomi ramulus*", "mixture", "allergic disease", and "prevention" are as described above.

The health functional food of the present invention is provided in various types of food additives or functional foods. Specifically, the health functional food may be processed into leached teas, liquid teas, beverages, fermented milk, cheese, yogurt, juices, probiotic preparations, health supplements, etc. which contain the composition, and may be used in the form of various food additives.

As used herein, the term "improvement" refers to all actions by which symptoms of an allergic disease are improved or beneficially altered by administering the composition.

The health functional food of the present invention may be one which further contains a sitologically acceptable carrier.

There is no particular limitation on the kind of food to which the composition containing the mixed extract of the present invention can be added, and it may include, for example, various beverages, gums, teas, vitamin complexes, supplementary health food, etc. Other ingredients that do not interfere with the effect of improving an allergic disease may be added to the food composition, and the kind thereof is not particularly limited. For example, as in ordinary foods, the composition may contain various herbal extracts, sitologically acceptable food additives, natural carbohydrates, etc. as an additional component.

The supplementary food additive is one which is added in preparing health functional food for each formulation and may be appropriately selected and used by those skilled in the art. For example, the supplementary food additive may include various nutrients, vitamins, minerals (electrolytes), flavoring agents (e.g., synthetic flavors and natural flavoring agents), coloring couplers and fillers, pectic acid and salts thereof, alginic acid and salts thereof, organic acids, protective colloidal thickeners, pH adjusting agents, stabilizing agents, preservatives, glycerin, alcohol, carbonating agents used in carbonated beverages, etc., and the kind of supplementary food additive is not limited by these examples.

In particular, the content of the extract contained in the food is not particularly limited, but may be contained in an amount of 0.01 wt % to 100 wt %, specifically 1 wt % to 80 wt % based on the total weight of the food composition.

When the food is beverage, it may be contained at a ratio of 1 g to 30 g, specifically 3 g to 20 g based on 100 mL. Additionally, the composition may contain additional ingredients that are commonly used in food compositions to improve odors, tastes, visual properties, etc. For example, vitamins A, C, D, E, B1, B2, B6, B12, niacin, biotin, folate, panthotenic acid, etc. may be contained. Additionally, it may contain minerals (e.g., zinc (Zn), iron (Fe), calcium (Ca), chromium (Cr), magnesium (Mg), manganese (Mn), copper (Cu), etc.). Additionally, amino acids (e.g., lysine, tryptophan, cysteine, valine, etc.) may be contained. Additionally, preservatives (potassium sorbate, sodium benzoate, salicylic acid, sodium dehydroacetate, etc.), disinfectants (bleaching powder and highly bleaching powder, sodium hypochlorite, etc.), antioxidants (butylhydroxyanisole (BHA), butylhydroxytoluene (BHT), etc.), coloring couplers (tar color, etc.), color fixing agents (sodium nitrate, etc.), bleaching agents (sodium sulfite), seasoning agents (MSG sodium glutamate, etc.), sweeteners (e.g., dulcin, cyclamate, saccharin, sodium, etc.), flavoring agents (vanillin, lactones, etc.), blowing agents (alum, potassium D-bitartrate, etc.), fortifying agents, emulsifying agents, thickening agents, coating agents, gum bases, antifoaming agents, solvents, improving agents, etc. The additives are selected according to food types and are used in suitable amounts.

The health functional food of the present invention may be prepared by a method commonly used in the art, and may be prepared by adding raw materials and ingredients commonly used in the art. Further, unlike other common drugs, the health functional food may be prepared using foods as raw materials, and thus the health functional food has advantages in that it can avoid side effects that may occur during long-term administration of drugs and that it provides excellent portability.

Still another aspect of the present invention provides a feed composition for prevention or improvement of an allergic disease, which contains a mixed extract of two or more selected from the group consisting of *Asiasarum* root, *Platycodon* root, and *Cinnamomi ramulus* as an active ingredient.

The terms "*Asiasarum* root", "*Platycodon* root", "*Cinnamomi ramulus*", "mixture", "allergic disease", "prevention", and "improvement" are as described above.

The feed composition may contain a feed additive. The feed additive of the present invention is classified as a supplementary additive according to the Control of Livestock and Fish Feed Act.

As used herein, the term "feed" may refer to any natural or artificial diet, meal, etc., or components of such meal which is intended to be eaten, ingested, or digested by animals or suitable therefor.

The kind of feed is not particularly limited, but any feed commonly used in the art may be used. Non-limiting examples of the feed may include plant-based feeds such as grains, root fruits, by-products of food processing, seaweeds, fibers, drug by-products, fats and oils, starches, meals, grain by-products, etc.; and animal-based feeds such as proteins, inorganic matters, fats and oils, minerals, single cell proteins, zooplanktons, foods, etc. These may be used alone or in a mixture of two or more thereof.

DETAILED DESCRIPTION OF THE INVENTION

Hereinafter, the constitutions and effects of the present invention will be described in more detail with reference to the following Examples. However, these Examples are for illustrative purposes only and the scope of the invention is not limited by these Examples.

Example 1. Preparation of Mixed Extract of Two or More Kinds Among *Asiasarum* Root, *Platycodon* Root, and *Cinnamomi ramulus*

*Asiasarum* root, *Platycodon* root, and *Cinnamomi ramulus* were each washed, and then dried completely. Each sample was added into a pulverizer and pulverized and extracted twice with 70% ethanol at 60° C. to 70° C. for 3 hours under reduced pressure to obtain a 70% ethanol extract and then freeze-dried. Each dried herbal extract was prepared at the following weight ratio (*Asiasarum* root: *Platycodon* root:*Cinnamomi ramulus*=1:2:2) to obtain BS012. Additionally, mixed extracts (in which *Asiasarum* root and *Platycodon* root are mixed at a 1:2 weight ratio; *Asiasarum* root and *Cinnamomi ramulus* are mixed at a 1:2 weight ratio; and *Platycodon* root and *Cinnamomi ramulus* are mixed at a 2:2 weight ratio) were prepared in the same manner.

Comparative Example 1. Preparation of Single Extract of *Asiasarum* Root, *Platycodon* Root, or *Cinnamomi ramulus*

In order to compare the effects of each extract, single extracts for each of *Asiasarum* root, *Platycodon* root, and *Cinnamomi ramulus* were prepared in the same manner as in Example 1.

Example 2. Preparation of Animal Model with Bronchial Asthma

A mouse model with bronchial asthma was prepared using the following method. First, for sensitization, 75 μg of ovalbumin (OVA) emulsified with 2 μL of aluminum hydroxide dissolved in 100 μL of PBS was administered intraperitoneally to a mouse and the mouse was sensitized twice on day 0 and day 14. After the second sensitization, bronchial asthma was induced in the mouse for challenge by administering 50 μg of OVA through systemic inhalation exposure over four times between day 27 and day 30.

In addition, in the case of the experimental group, BS012 obtained in Example 1 was administered intratracheally at various concentrations (1.5 mg/head, 5 mg/head, 15 mg/head, and 50 mg/head) at the same time point as the four challenges.

Experimental Example 1. Analysis of Bronchial Leachate and Serum IgE from Bronchial Asthma Model Treated with Mixed Extract 1-1. Analysis of Bronchial Leachate and Serum IgE According to Trachea Exposure of BS012

In order to confirm the effects of the mixed extract on bronchial asthma, the levels of IL-4 and IL-5 (which are cytokines produced by T helper type 2 (Th2) cells and have an important mediating role in trachea hypersensitivity and an eosinophilic inflammatory response in bronchial asthma), IFN-γ (which is a cytokine mediated by Th1 cells and affects autoimmunity), and IgE (which acts at the basic stage in an inflammatory response) were analyzed.

After washing the trachea of the animal model of Example 2 by inserting a catheter thereinto and injecting 1 mL of Dulbecco's Phosphate-Buffered Saline (dPBS) thereto, 0.75 mL of bronchoalveolar lavage fluid (BALF) was obtained. The obtained BALF was centrifuged at 5,000 rpm at 4° C. for 10 minutes to obtain a supernatant to be used for cytokine analysis, which was frozen and stored at −20° C. In the case of serum, blood was obtained from each mouse, reacted at room temperature for 30 minutes, and centrifuged to obtain serum.

The concentrations of the Th2 cytokines (IL-4 and IL-5) and Th1-mediated cytokine (IFN-γ) present in BALF were quantified using an ELISA kit. Each of BALF (50 μL) was added to a well plate, which was coated in advance with anti-IL-4, anti-IL-5, and anti-IFN-γ antibodies, respectively, and the well plate was incubated at room temperature for 2 hours and then washed three times with washing buffer. Thereafter, 100 μL each of mouse IL-4, IL-5, and IFN-γ conjugates was added thereto, and the resultants were incubated at room temperature for 2 hours and then washed three times. Finally, 100 μL of a termination solution was added to stop the reaction. The level of IgE in serum was also confirmed by ELISA.

The absorbance of cytokines and serum IgE in the plate detected by the above method was measured at 450 nm with a microplate reader.

As a result, as shown in FIG. 1, it was confirmed that while the levels of IL-4 and IL-5 were significantly reduced by the treatment of BS012, the level of IFN-γ was not affected by BS012, in the analysis results of bronchial leachate and serum IgE according to trachea exposure of BS012 at various concentrations (i.e., 1.5 mg/head (T1), 5 mg/head (T2), 15 mg/head (T3), and 50 mg/head (T4)). Additionally, it can be seen that the level of IgE was significantly reduced by BS012.

In the above, although BS012 showed a tendency of inhibiting an inflammatory response by inhibiting IgE, the levels of IL-4 and IL-5 produced by Th2 were decreased, whereas the level of IFN-γsms produced by Th1 mediation was not affected. Therefore, it can be determined that BS012 specifically affected the Th2 mechanism.

1-2. Analysis of Levels of Bronchial Leachate and Serum IgE According to Nasal Inhalation Exposure of BS012

In order to confirm the difference in effect according to the administration route of BS012, an animal model with bronchial asthma was prepared in the same manner as in Example 2. In the case of the experimental group, BS012 obtained in Example 1 was administered at various concentrations (9 mg/m$^3$, 27 mg/m$^3$, and 80 mg/m$^3$) 3 hours before the exposure to a bronchial asthma-inducing material through nasal inhalation exposure at the same time point as the four challenges. As the positive control group, 1.5 mg/kg of dexamethasone was administered intraperitoneally 1 hour before exposure to the bronchial asthma-inducing material.

The levels of BALF and serum IgE were analyzed in the same manner as in Experimental Example 1-1.

As a result, as shown in FIG. 2, it was confirmed that while the levels of IL-4, IL-5, and IL-13 (which are cytokines produced by Th2) were significantly reduced by the treatment of BS012, the levels of IFN-γ and IL-17 (which are cytokines mediated by Th1 and Th17) did not show any significant effect according to the concentration of BS012, in the analysis results of bronchial leachate and serum IgE according to nasal inhalation exposure of BS012 at various concentrations (i.e., 9 mg/head (T1), 27 mg/head (T2), and 80 mg/head (T3)) and dexamethasone at a concentration of 1.5 mg/kg (T4).

From these results, it can be determined that even if BS012 is treated in the form of nasal inhalation exposure, BS012 can still exhibit a Th2 mechanism-specific inhibitory effect.

Experimental Example 2. Analysis of Effect of Mixed Extract on Inhibiting Cell Differentiation of T Cells It is well known that Th2 affects bronchial asthma among the mechanisms of immune responses. In this regard, in order to confirm the effect of a mixed extract of two or more among *Asiasarum* root, *Platycodon* root, and *Cinnamomi ramulus* on the cell differentiation process of T cells, the differentiation levels of Th1, Th2, and Th17 involved in immune responses were analyzed. Additionally, for the comparison of effects among the extracts, mixed extracts of two or more among *Asiasarum* root, *Platycodon* root, and

*Cinnamomi ramulus* and single extracts thereof obtained in Example 1 and Comparative Example 1 were treated and their effects were analyzed.

2-1. Analysis of Level of Th1 Cell Differentiation

Bone marrow cells were obtained by separating the femur and tibia of each mouse and then allowed to differentiate in an RPMI-1640 medium (10% fetal bovine serum, 1% penicillin/streptomycin, and 25 mM HEPES), which contains 20 ng/mL of GM-CSF, for 7 to 8 days to thereby obtain dendritic cells. The spleen and lymph nodes of each mouse were crushed into a 100 μm mesh to prepare single cells, and then positive selection was performed using CD4 microbeads. Thereafter, CD4$^+$CD62L$^{hi}$CD25-CD44$^{lo}$ population (naive CD4$^+$ T cells) was isolated using the BD FACS ARIA III. For differentiation into Th1, a vehicle or test material was treated to a medium containing α-CD3 (2 μg/mL), lipopolysaccharides (300 ng/mL), and α-IL-4 (5 μg/mL), and then dendritic cells (1×10$^4$) and naive CD4$^+$ T cells (1×10$^5$) were added thereto and the mixture was cultured for 72 hours. Thereafter, the resultant was treated with phorbol myristate acetate (100 ηM), ionomycin (1 μg/mL), brefeldin A (5 μg/mL), and monensin (2 μM). After 4 hours, cells were obtained, fixed, and stained for intracellular cytokines. The resulting cells were detected using BD FACS LSR Fortessa and analyzed using FlowJo™ software.

As a result, as shown in FIG. 3, it was confirmed that BS012 showed no inhibitory effect against the differentiation of Th1 under the conditions where the differentiation of CD4$^+$ T cells into Th1 is promoted. Among the mixed extracts containing two of *Asiasarum* root, *Platycodon* root, and *Cinnamomi ramulus*, the mixed extract (*Platycodon* root and +*Asiasarum* root) showed a significant inhibitory effect, but it was at a negligible level, and each single extract of *Asiasarum* root, *Platycodon* root, and *Cinnamomi ramulus* showed about a 30% inhibitory effect against the differentiation.

The inhibitory effect against the differentiation when treated with each single extract appears to be due to the high concentration of each individual material compared to the mixture.

2-2. Analysis of Level of Th2 Cell Differentiation

Dendritic cells and naive CD4$^+$ T cells were obtained in the same manner as in Th1. For differentiation into Th2, a vehicle or test material was treated to a medium containing α-CD3 (2 μg/mL), IL-2 (20 ng/mL), IL-4 (10 ng/mL), and α-IFNγ (5 μg/mL), and then dendritic cells (1×10$^4$) and naive CD4$^+$ T cells (1×10$^5$) were added thereto and the mixture was cultured for 72 hours. Thereafter, the resultant was treated with phorbol myristate acetate (100 nM), ionomycin (1 μg/mL), brefeldin A (5 μg/mL), and monensin (2 μM). After 4 hours, cells were obtained, fixed, and stained for intracellular cytokines. The resulting cells were detected using BD FACS LSR Fortessa and analyzed using FlowJo™ software.

As a result, as shown in FIG. 4, it was confirmed that BS012 showed the most excellent inhibitory effect against the differentiation of Th2 under the conditions where the differentiation of CD4$^+$ T cells into Th2 is promoted. The mixed extracts containing two of *Asiasarum* root, *Platycodon* root, and *Cinnamomi ramulus*, except the mixed extract (*Platycodon* root+*Cinnamomi ramulus*), were shown to have the second highest inhibitory effect against the differentiation. Even in single extracts, except *Cinnamomi ramulus*, both an *Asiasarum* root extract and a *Platycodon* root extract showed significant inhibitory effects against the differentiation. Through the increase in the effects of inhibiting the Th2 differentiation of the mixtures of two and three of *Asiasarum* root, *Platycodon* root, and *Cinnamomi ramulus* at the same concentration compared to the effects of single extracts, it was confirmed that the mixture of each extract exhibited an additive effect.

2-3. Analysis of Level of Th17 Cell Differentiation

Dendritic cells and naive CD4$^+$ T cells were obtained in the same manner as in Th1. For differentiation into Th17, a vehicle or test material was treated to a medium containing α-CD3 (2 μg/mL), LPS (200 ng/mL), TGFβ (5 ng/mL), and α-IL-4 (5 μg/mL), α-IFNγ (5 μg/mL), and then dendritic cells (1×10$^4$) and naive CD4$^+$ T cells (1×10$^5$) were added thereto and the mixture was cultured for 72 hours. Thereafter, the resultant was treated with phorbol myristate acetate (100 nM), ionomycin (1 μg/mL), brefeldin A (5 μg/mL), and monensin (2 μM). After 4 hours, cells were obtained, fixed, and stained for intracellular cytokines. The resulting cells were detected using BD FACS LSR Fortessa and analyzed using FlowJo™ software.

As a result, as shown in FIG. 5, it was confirmed that all of the mixtures or single extracts showed no effect on the differentiation of Th17 under the conditions where the differentiation of CD4$^+$ T cells into Th17 is promoted.

Taken together, it was confirmed that BS012 exhibited a Th2-specific additive inhibitory effect against the differentiation, suggesting that BS012 may have a therapeutic effect on allergic diseases among immune responses, representatively allergic respiratory diseases.

Example 3. Preparation of Bronchial Asthma Model Orally Administered with Mixed Extract In order to confirm the anti-bronchial asthma effect in accordance with repeated oral administration of the mixed extract BS012, the mixed extract BS012 and dexamethasone (Dex), as a positive control, were orally administered once daily for 19 days according to Table 1 below.

In order to induce bronchial asthma in a mouse model simultaneously with oral administration, 75 μg of ovalbumin (OVA) emulsified with 2 μL of aluminum hydroxide dissolved in 100 μL of PBS was administered intraperitoneally to a mouse and the mouse was sensitized twice on day 0 and day 7. After the second sensitization, bronchial asthma was induced in the mouse for challenge by administering 50 μg of OVA through systemic inhalation exposure over four times between day 14 and day 17. The final oral administration was given to the mouse on day 19 and the mouse was autopsied the next day.

TABLE 1

| Experimental Groups | Number of Animals | Animal ID | Induction of Asthma | Test Drug | Dose (mg/kg/day) |
|---|---|---|---|---|---|
| Vehicle Control | 6 | 1-6 | X | — | — |
| Test Drug-1 (T1) | 6 | 7-12 | ○ | BS012 | 50 |
| Test Drug-2 (T2) | 6 | 13-18 | ○ | BS012 | 100 |
| Test Drug-3 (T3) | 6 | 19-24 | ○ | BS012 | 200 |
| Control Drug (T4) | 6 | 25-30 | ○ | Dex | 1.5 |
| Asthma Control | 6 | 31-36 | ○ | — | — |

Figure 6:
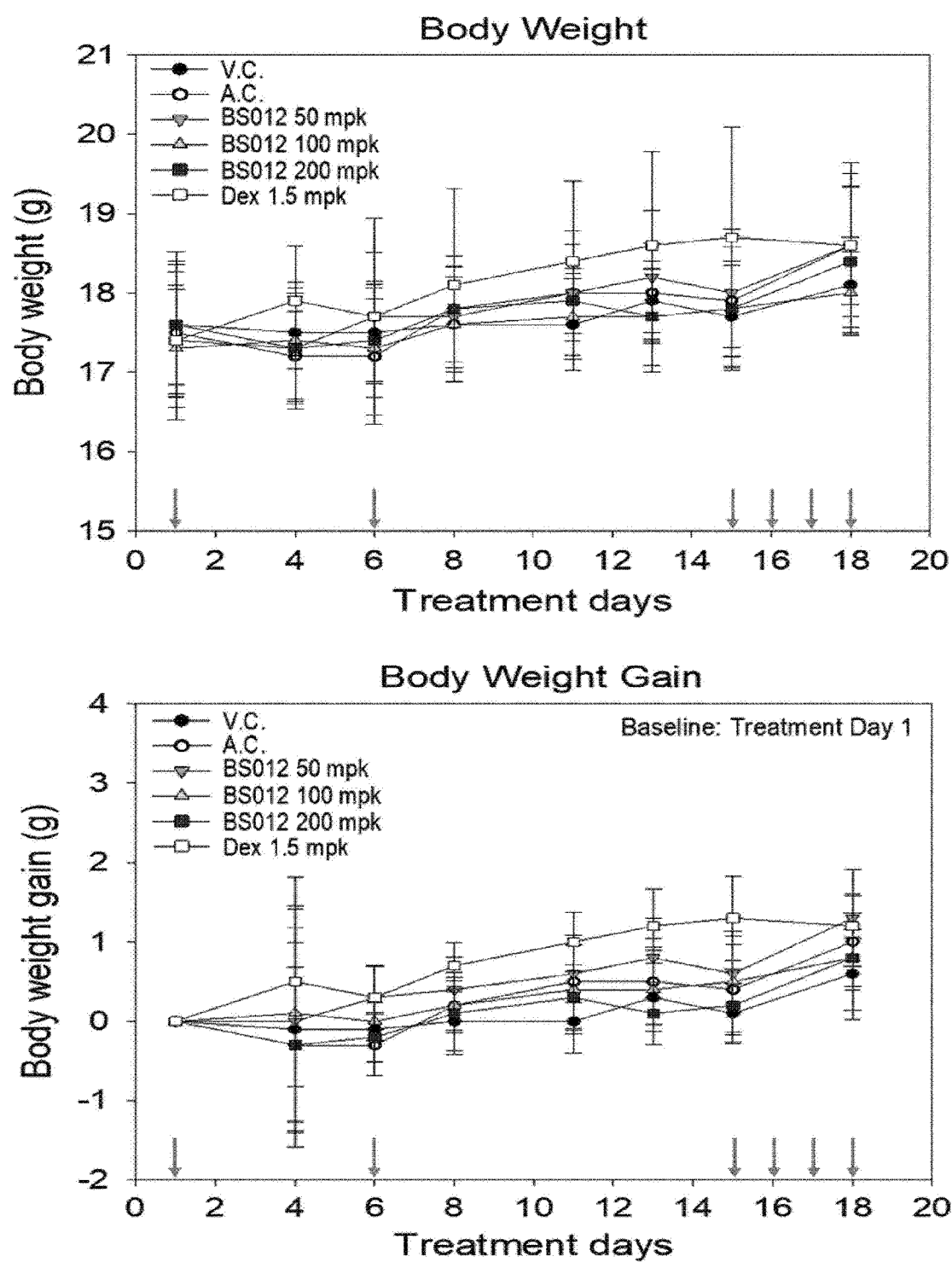
FIG. 6 shows graphs illustrating the changes in body weight of a bronchial asthma model according to the treatment with an extract of each of *Asiasarum* root, *Platycodon* root, and *Cinnamomi ramulus*, and a mixture thereof.

Experimental Example 3. Analysis of Anti-Bronchial Asthma Effect in Bronchial Asthma Model by Oral Administration of Mixed Extract 3-1. Analysis of Changes in Body Weight The body weight of a bronchial asthma model was measured two to three times a week during the period of oral administration of the mixed extract. As a result, it was confirmed that the oral administration of the mixed extract and other experimental groups did not show any significant effect on weight gain/reduction in the bronchial asthma model, as shown in FIG. 6.

3-2. Analysis of Changes in Organ Weight

Figure 7:
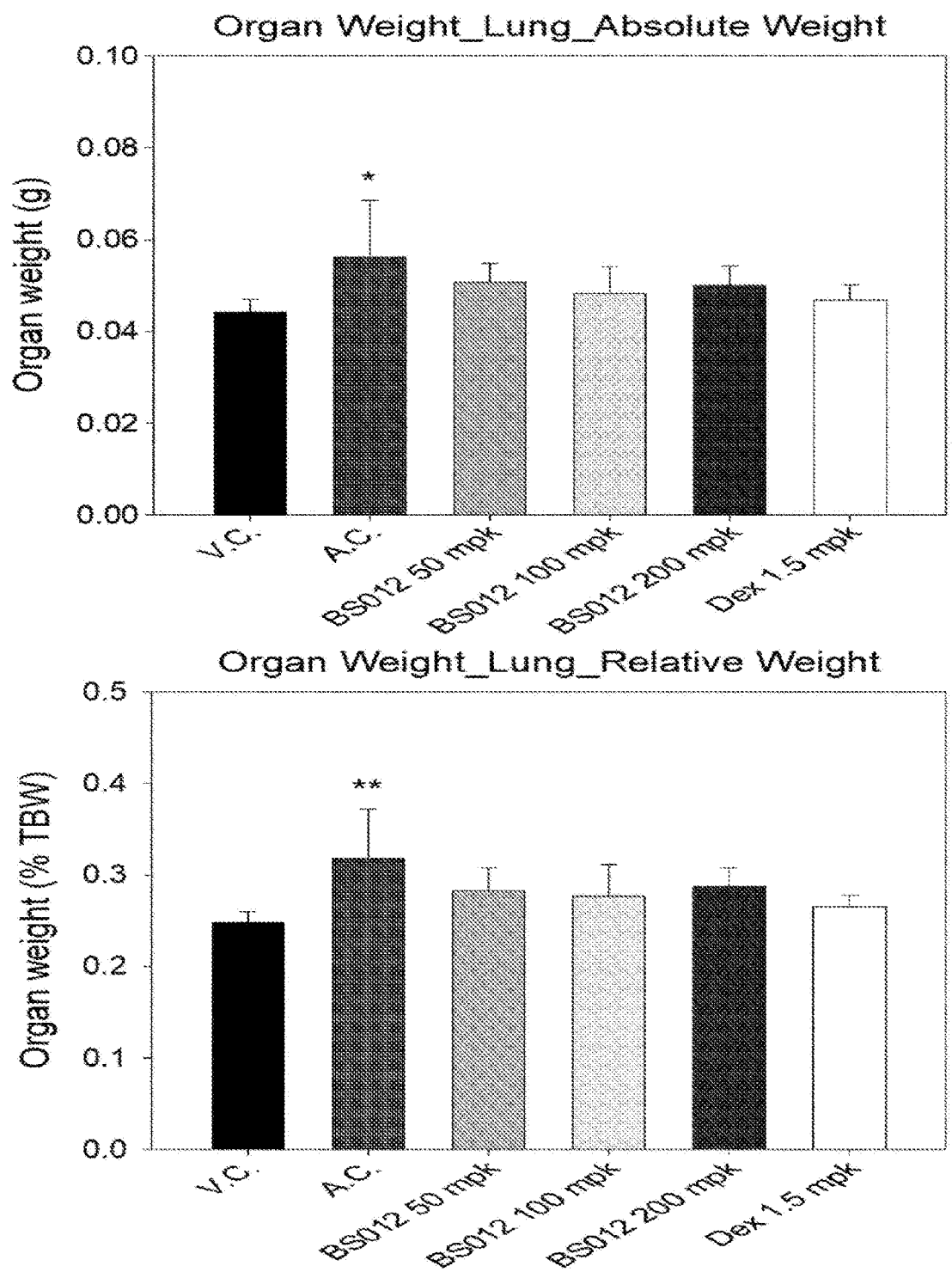
FIG. 7 shows graphs illustrating the changes in lung weight of a bronchial asthma model according to the treatment with an extract of each of *Asiasarum* root, *Platycodon* root, and *Cinnamomi ramulus*, and a mixture thereof.

The left lung lobe of the animal models was extracted and its weight was measured. As a result, as shown in FIG. 7, it was confirmed that the weight of the left lung lobe of the animal model was lower than that of the bronchial asthma control, and there was no significant difference between the groups administered with the mixed extracts.

3-3. Analysis of Levels of Serum IgE, Cytokines, and Th2 Cell Differentiation

The levels of BALF and serum IgE of samples collected from the right lung lobe were analyzed in the same manner as in Experimental Example 1-1.

Figure 8:
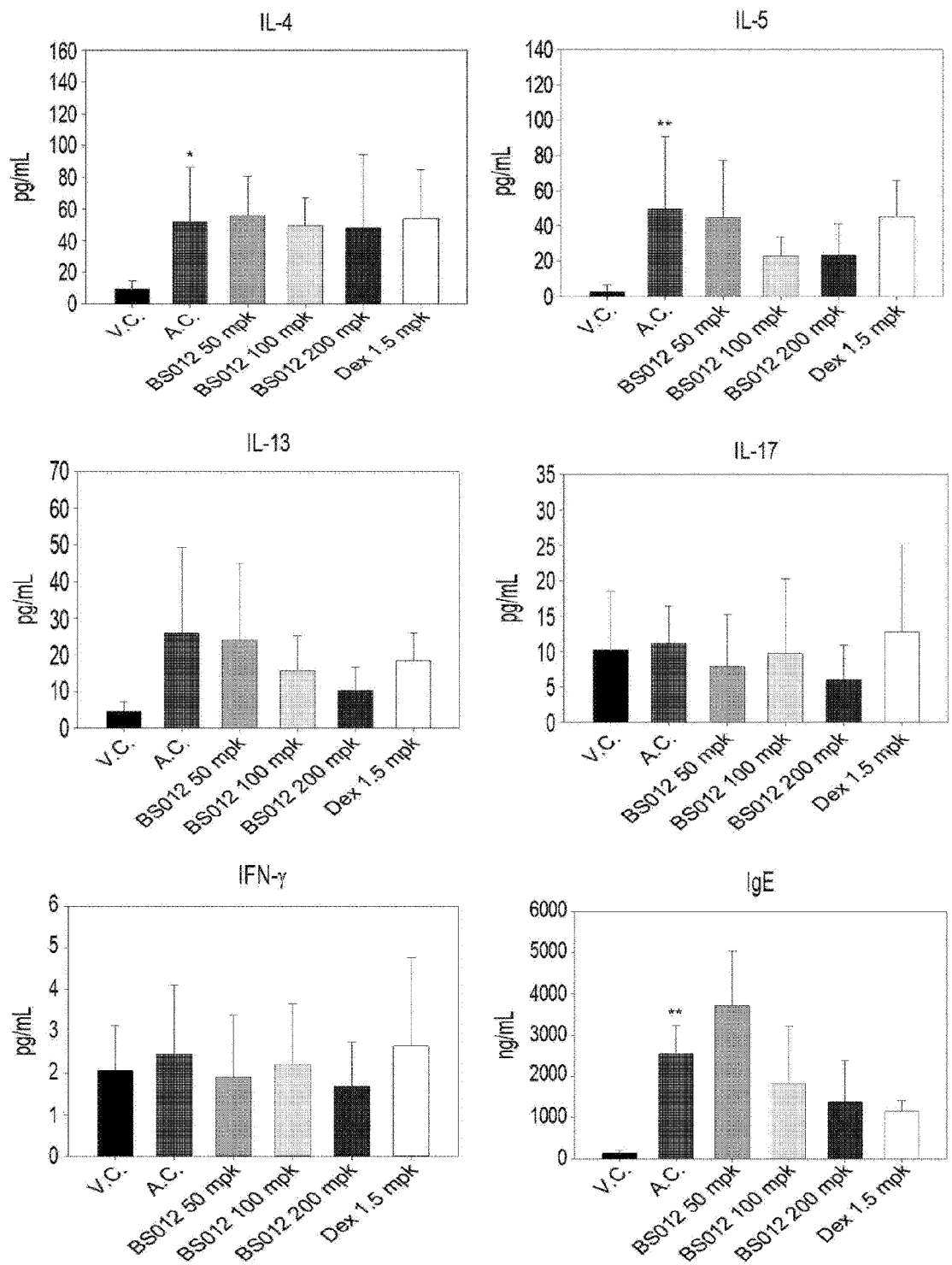
FIG. 8 shows graphs illustrating the analysis results of serum IgE and cytokines according to the treatment with an extract of each of *Asiasarum* root, *Platycodon* root, and *Cinnamomi ramulus*, and a mixture thereof.

As a result, as shown in FIG. 8, it was confirmed that IL-5 and IL-13 (i.e., cytokines produced by Th2) and IFN-γ and IL-17 (i.e., cytokines mediated by Th1 and Th17) showed a significant reduction by BS012 treatment. In particular, it was confirmed that IgE showed a significant effect according to its concentration.

Figure 9:
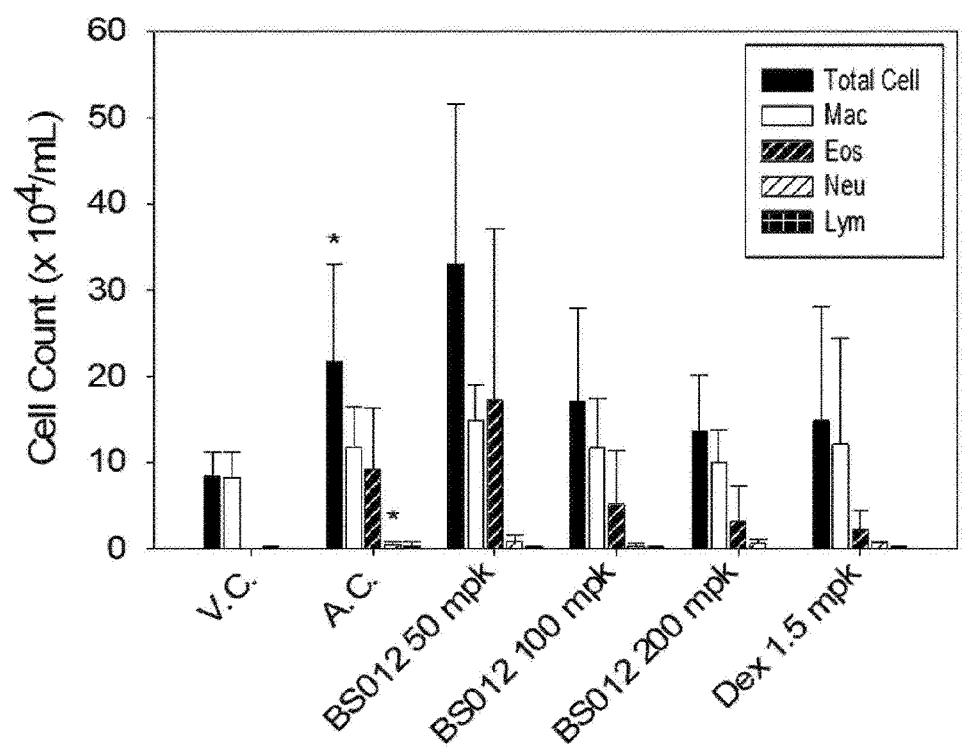
FIG. 9 shows a graph illustrating the calculation results of leukocyte percentage according to the treatment with an extract of each of *Asiasarum* root, *Platycodon* root, and *Cinnamomi ramulus*, and a mixture thereof.

Additionally, as a result of differential cell count of white blood cells, it was confirmed that BS012 inhibited a Th2-selective response during the process of T cell differentiation, and that BS012 administration at a dose of 200 mg/kg showed an activity equal to or higher than that of dexamethasone, as shown in FIG. 9.

Taken together, it was confirmed that in the bronchial asthma model induced by OVA, BS012 showed a tendency to inhibit influx of eosinophils and Th2 responses in a dose-dependent manner not only during inhalation but also during oral administration. In particular, it was confirmed that the BS012 administration at a dose of 200 mg/kg showed an activity equal to or higher than that of dexamethasone (i.e., a strong steroid), suggesting that BS012 may be used as a natural drug candidate to replace the adrenal corticosteroid drug in the existing market of bronchial asthma control agents.

In light of the remarkable inhibitory effect of IgE in blood, BS012 was considered to be applicable to other Th2-mediated immune diseases (e.g., atopic dermatitis, etc.), and thus, the effect of BS012 on atopic dermatitis was tested thereafter.

Example 4. Preparation of Atopic Dermatitis Model Orally Administered with Mixed Extract NC/Nga mice were purchased from Central lab Animal Inc. (Seoul, Korea) and were bred to 12 weeks of age under constant temperature (23±3° C.), humidity (55±15%), and amount of radiation (12 hours).

2,4-dinitrochlorobenzene (DNCB) is a drug inducing atopic dermatitis and was purchased from Sigma Chemical Co. (St. Louis, MO, USA). DNCB was used after diluting to concentrations of 0.5% and 1% in a 3:1 mixture of acetone and olive oil. 5 days before the start of the experiment, the back of each mouse was depilated, and then left for 24 hours to heal microscopic wounds on the skin. 200 μL of 1% DNCB solution was applied to the back area and an immune response was induced for 4 days, and 200 μL of 0.5% DNCB solution was applied to the back area for 6 weeks to induce atopic dermatitis.

Thereafter, the mixed extract BS012 (K6922; 50 mg/kg/day (low, L), 100 mg/kg/day (medium, M), and 200 mg/kg/day (high, H)) or dexamethasone (Dex; 0.5 mg/kg/day), as a positive control, was orally administered to the atopic dermatitis-induced animal model once daily for 10 days using a tube.

Figure 10:
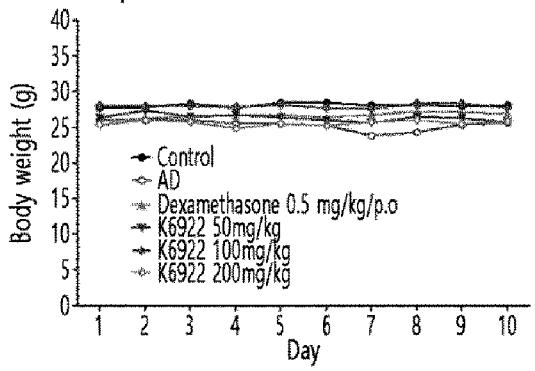
FIG. 10 shows graphs illustrating the changes in body weight and the weight of liver, spleen, and kidney of an atopic dermatitis model according to the treatment with an extract of each of *Asiasarum* root, *Platycodon* root, and *Cinnamomi ramulus*, and a mixture thereof.
Figure 10:
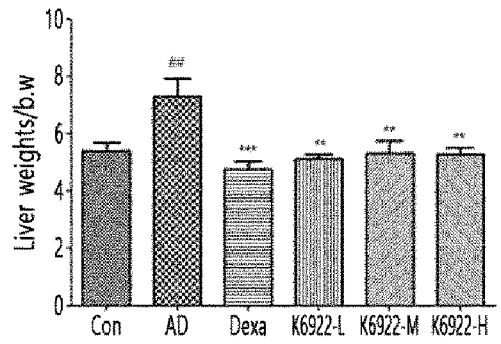
Figure 10:
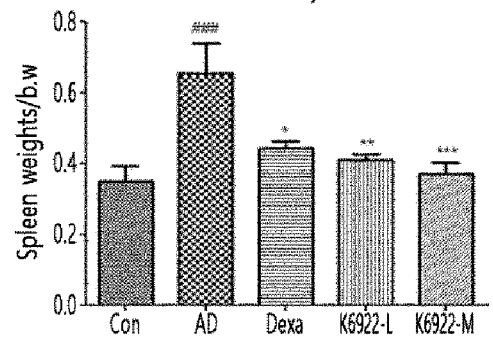
Figure 10:
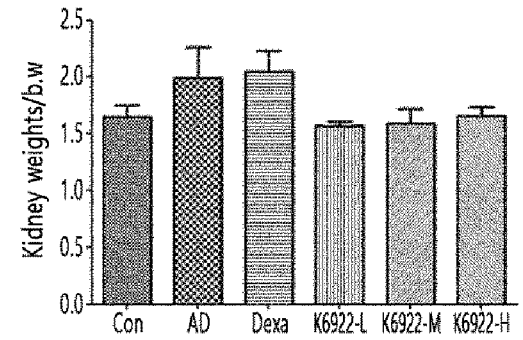
Figure 10:
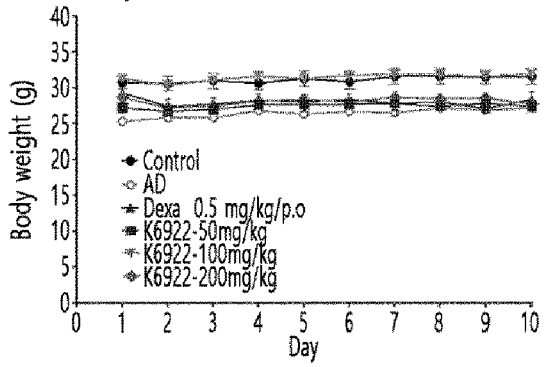
Figure 10:
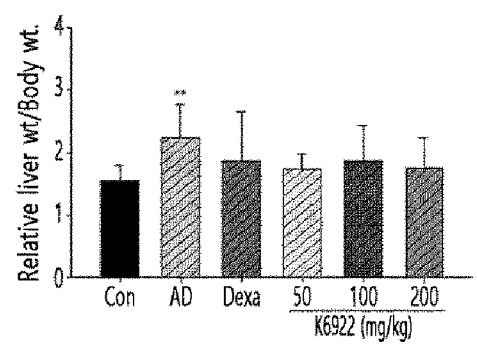
Figure 10:
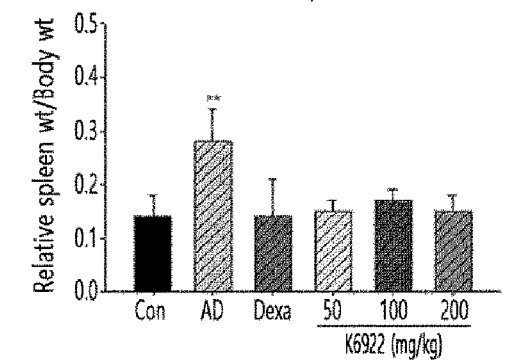
Figure 10:
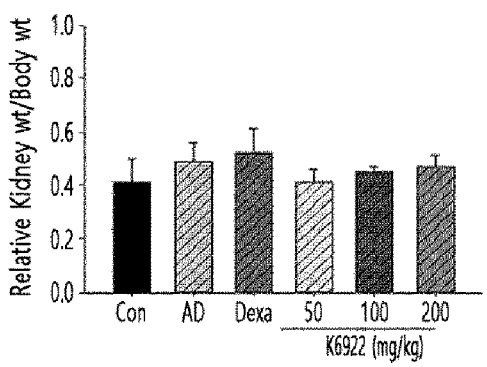

Experimental Example 4. Analysis of Effect According to Oral Administration of Mixed Extract on Improvement of Atopic Dermatitis in Atopic Dermatitis Model 4-1. Analysis of Changes in Body Weight The body weight of the atopic dermatitis model was measured two to three times a week during the period of oral administration of the mixed extract. As a result, as shown in FIG. 10, it was confirmed that the oral administration of the mixed extract and other experimental groups did not show any significant effect on weight gain/reduction in the atopic dermatitis model.

4-2. Observation of Skin Surface

Figure 11:
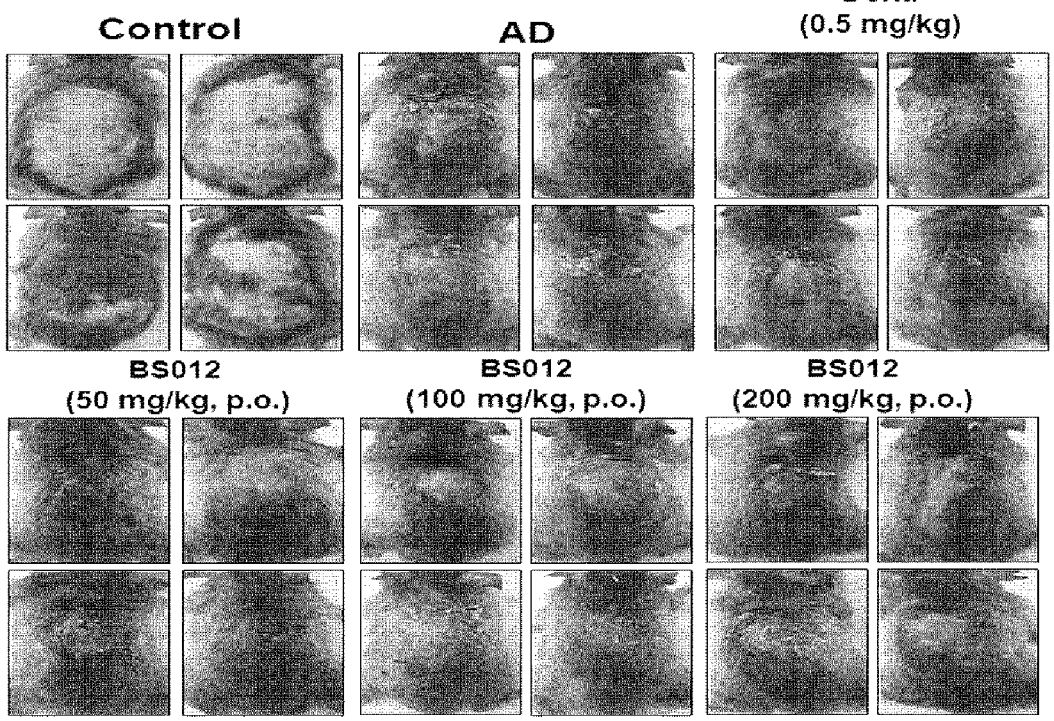
FIG. 11 shows images illustrating the changes in skin surface of an atopic dermatitis model according to the treatment with an extract of each of *Asiasarum* root, *Platycodon* root, and *Cinnamomi ramulus*, and a mixture thereof.
Figure 11:
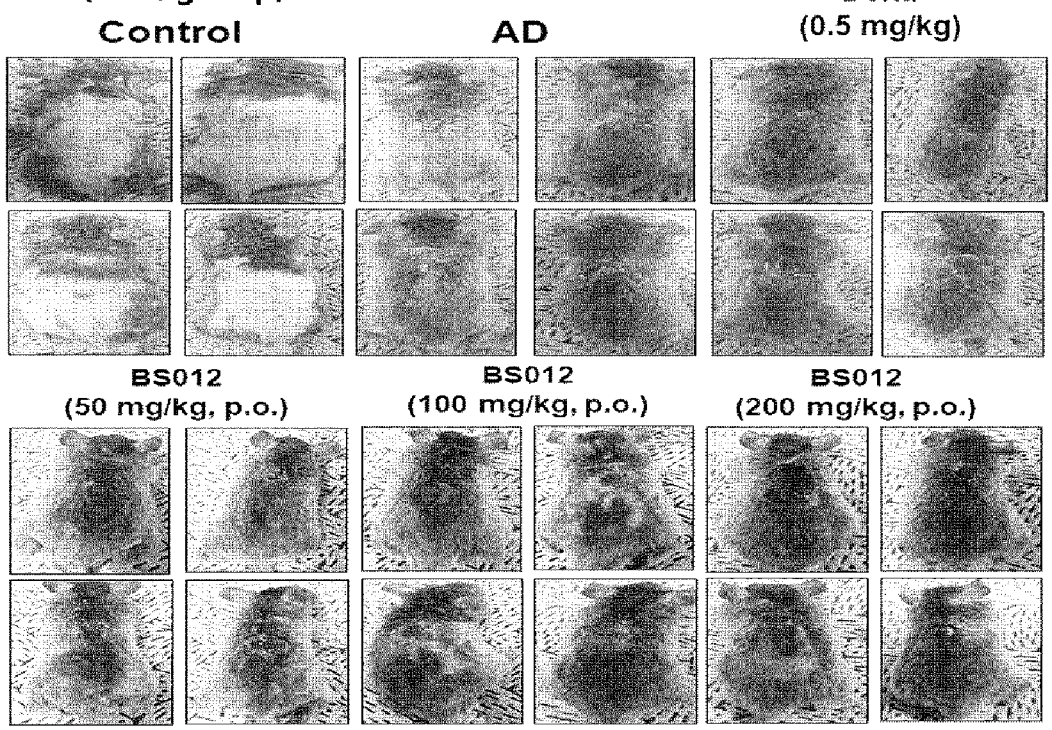
Figure 12:
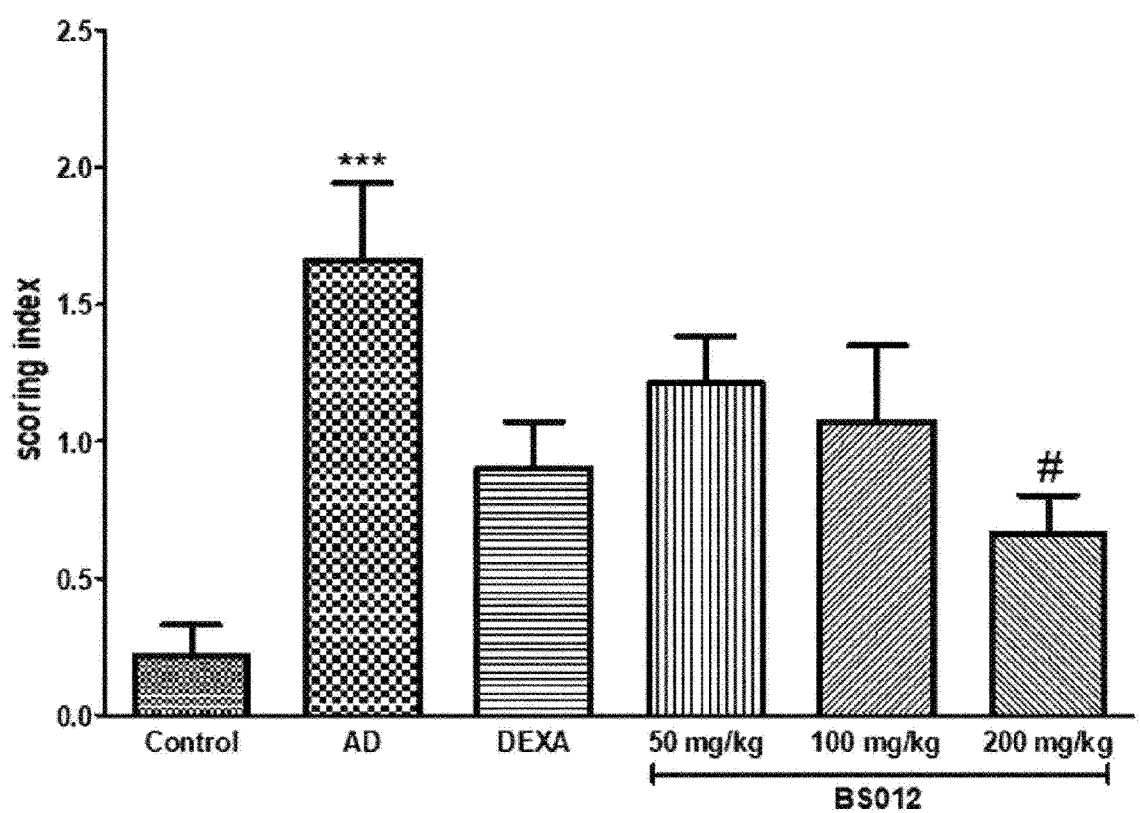
FIG. 12 shows a graph illustrating the scoring index on skin surface of an atopic dermatitis model according to the treatment with an extract of each of *Asiasarum* root, *Platycodon* root, and *Cinnamomi ramulus*, and a mixture thereof (Control: a control group in which atopic dermatitis is not induced and no treatment is made; and AD: a control group in which atopic dermatitis is induced but no treatment is made).

The skin surface of the atopic dermatitis model was observed on day 1, day 3, day 5, and day 10 during the period of oral administration of the mixed extract. As a result, as shown in FIGS. 11 and 12, it was confirmed that severe skin damage associated with atopic dermatitis occurred in the control group (AD), in which no treatment was made after the induction of atopic dermatitis, whereas skin damage was inhibited in the skin of mice in which the mixed extract BS012 was administered at a dose of 100 mg/kg/day and 200 mg/kg/day, respectively, and that the effect was shown to be equal to or higher than that of dexamethasone (i.e., positive control).

4-3. Analysis of Number of Scratches

Figure 13:
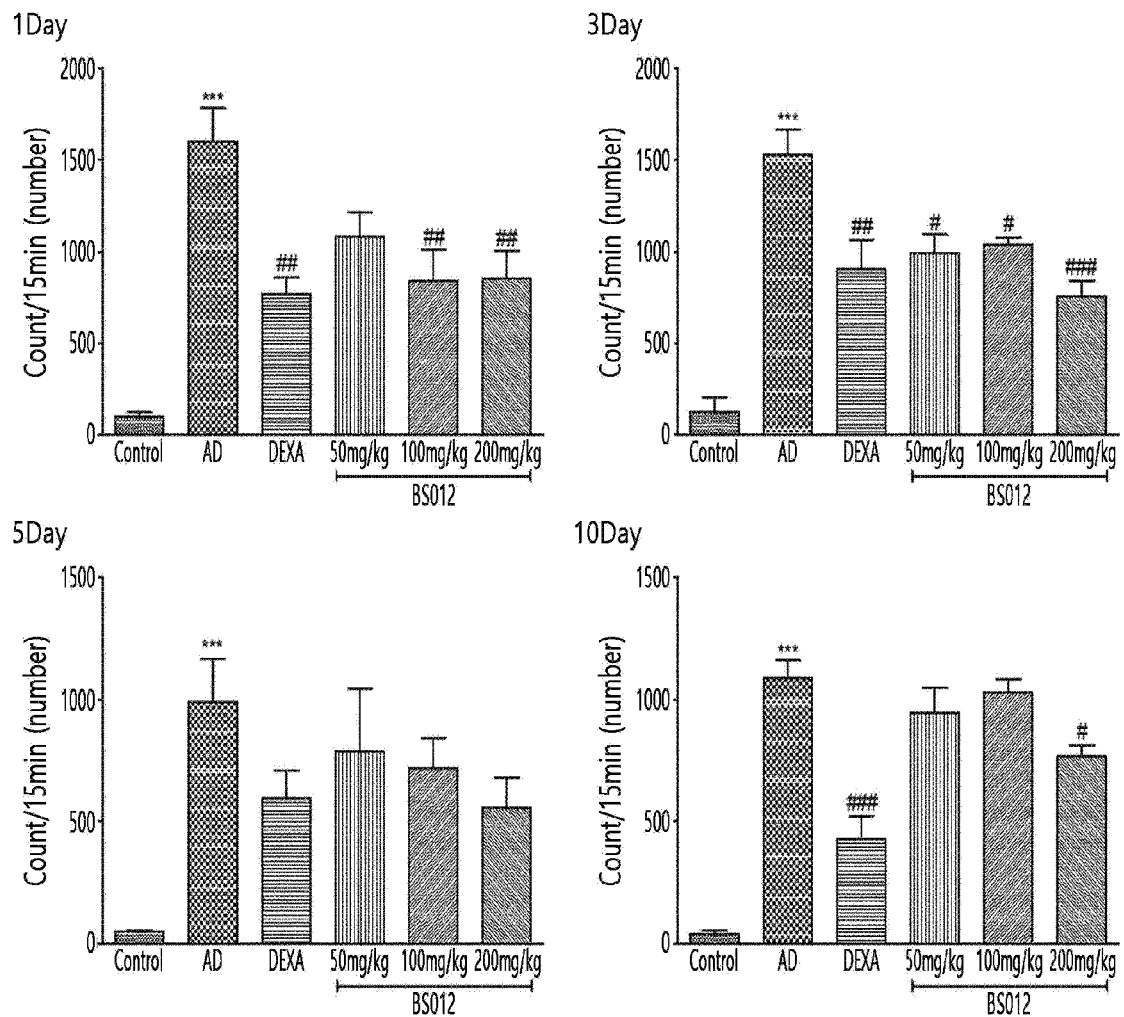
FIG. 13 shows graphs illustrating the number of scratches in the atopic dermatitis model according to the treatment with an extract of each of *Asiasarum* root, *Platycodon* root, and *Cinnamomi ramulus*, and a mixture thereof (Control: a control group in which atopic dermatitis is not induced and no treatment is made; and AD: a control group in which atopic dermatitis is induced but no treatment is made).

The number of scratches of the atopic dermatitis model was counted on day 1, day 3, day 5, and day 10 during the period of oral administration of the mixed extract. As a result, as shown in FIG. 13, it was confirmed that the number of scratches of the mice administered with BS012 at a dose of 100 mg/kg/day and 200 mg/kg/day, respectively, was decreased compared to the control group (AD), in which no treatment was made after the induction of atopic dermatitis.

4-4. Analysis of Levels of Serum IgE and Cytokines

A blood sample was obtained from the atopic dermatitis model and was reacted at room temperature for 30 minutes and then centrifuged to obtain serum.

The concentrations of serum IgE; IL-4 and IL-5 (i.e., Th2 cytokines); IFN-γ and IL-17 (i.e., Th1 and Th17-mediated cytokines); IL-6; and thymic stromal lymphopoietin (TSLP) (i.e., a cytokine which is known to cause a Th2 inflammatory response by inducing CD11c+ myeloid dendritic cells) were quantified using an ELISA kit. The analysis was performed using the same method as in Experimental Example 1-1.

As a result, as shown in FIG. 14, it was confirmed that while the control group (AD), in which no treatment was made after the induction of atopic dermatitis, showed an increase in the expression of serum IgE, IL-4, IL-5, and TSLP and a decrease in the expression of IFN-γ, and that the groups in which BS012 and dexamethasone were treated, respectively, showed an increase in the expression of IFN-γ while the expression of serum IgE, IL-4, IL-5, and TSLP was inhibited.

4-5. Analysis of Levels of Histopathological Changes in Skin

The skin tissue of the atopic dermatitis model was biopsied, fixed in formalin in 10% paraform-aldehyde for 24 hours, and then formatted with paraffin and prepared into 4 μM-thick blocks. The thus-isolated tissues were subjected to hematoxyline/eosin (H&E) staining, which is able to distinguish epidermis, dermis, keratinocytes, neutrophils, eosinophils, other cells, and edemas, and to toluidine blue staining, which is able distinguish mast cell infiltration by staining of mast cells, and the cells were observed under an optical microscope (BX51, Olympus, Japan, X100).

Figure 15:
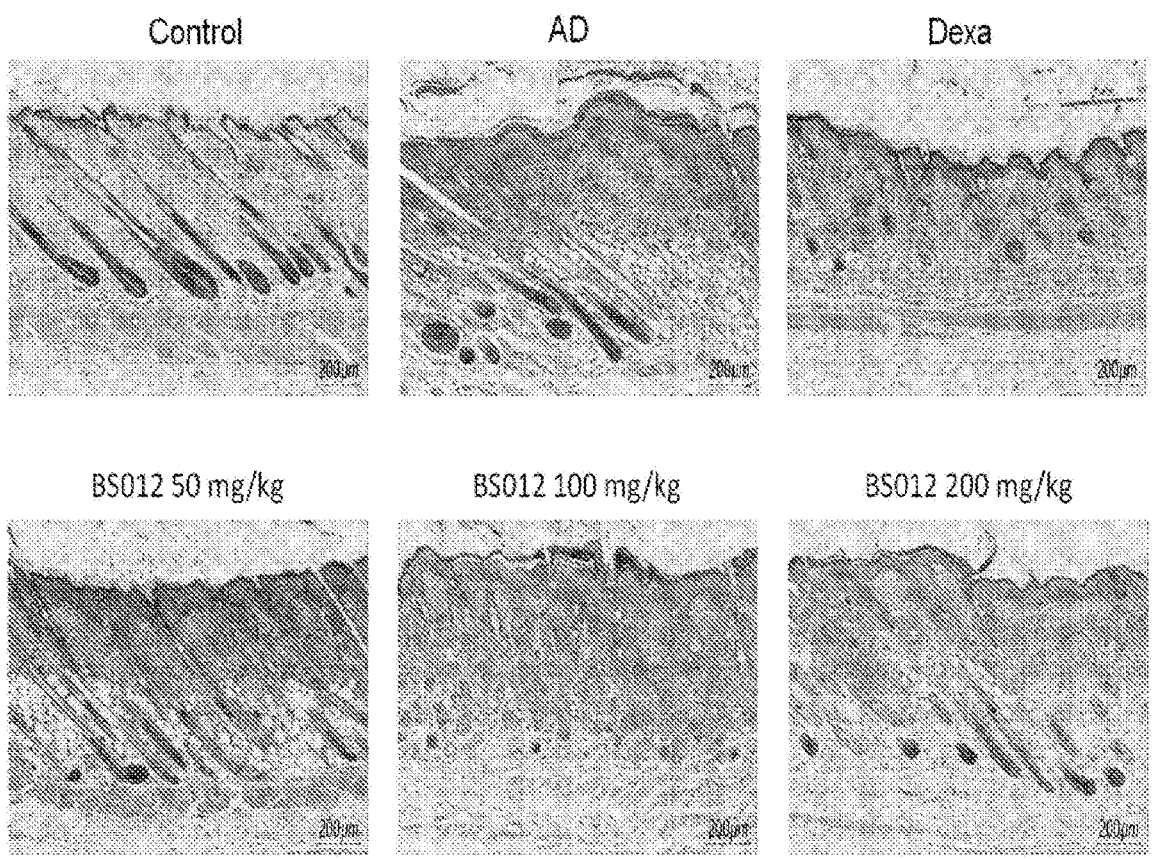
FIG. 15 shows H & E staining images of skin tissue according to the treatment with an extract of each of *Asiasarum* root, *Platycodon* root, and *Cinnamomi ramulus*, and a mixture thereof.
Figure 16:
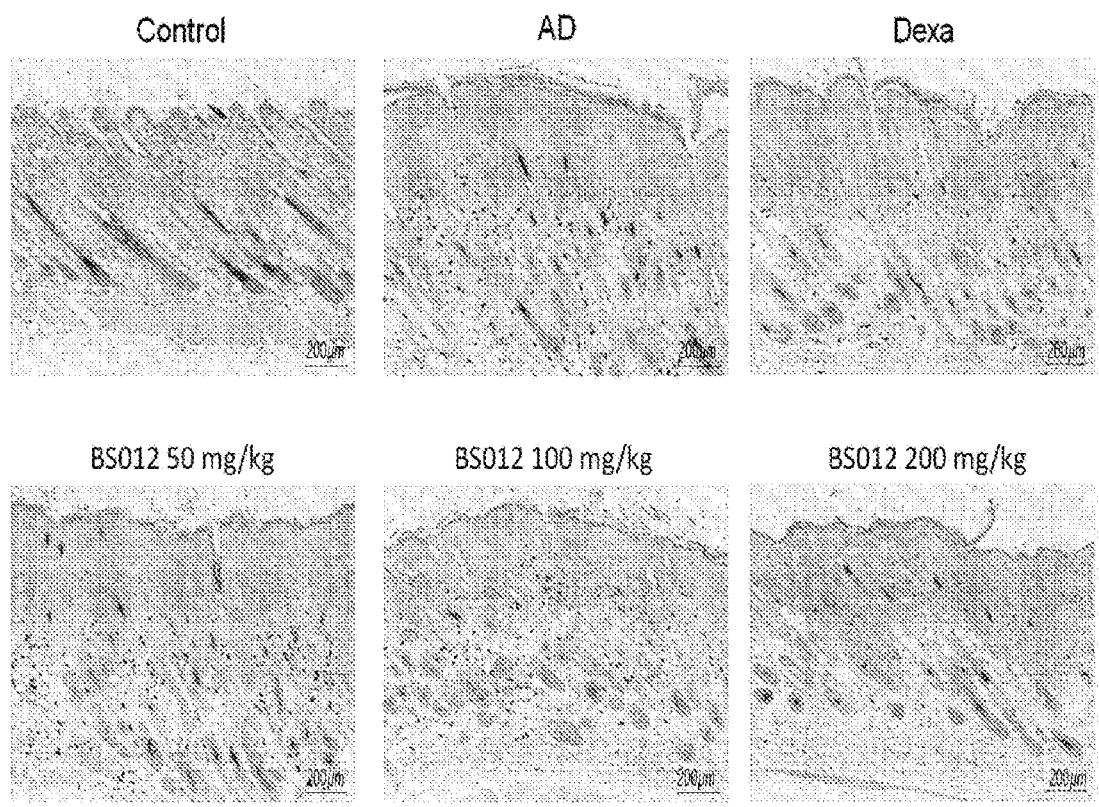
FIG. 16 shows Toluidine blue staining images of skin tissue according to the treatment with an extract of each of *Asiasarum* root, *Platycodon* root, and *Cinnamomi ramulus*, and a mixture thereof.
Figure 17:
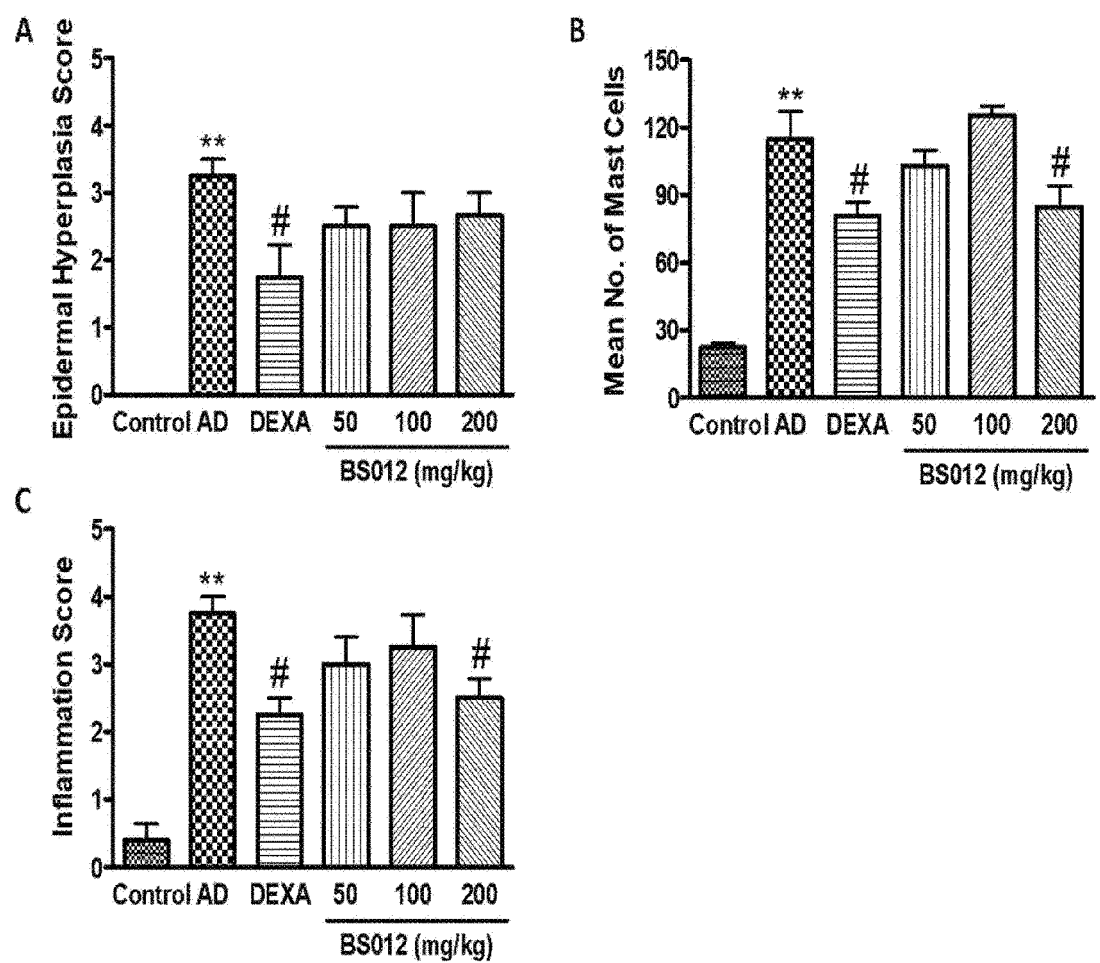
FIG. 17 shows graphs illustrating the levels of skin tissue with respect to (A) epidermal hyperplasia, (B) average number of mast cells, and (C) inflammation according to the treatment with an extract of each of *Asiasarum* root, *Platycodon* root, and *Cinnamomi ramulus*, and a mixture thereof.

As a result, it was confirmed that the atopic dermatitis model in the control group (AD), in which no treatment was made after the induction of atopic dermatitis, enlarged to make it hyperplasia in the epidermal thickness (FIG. 15) and increased remarkable in mast cell infiltration (FIG. 16), etc., compared to the normal group, whereas the atopic dermatitis model in the groups, in which BS012 and dexamethasone were treated, respectively, showed a remarkable decrease in the epidermal thickness and a decrease in mast cell infiltration compared to the control group. The same results as above were confirmed in FIG. 17, in which the results are shown in numerical values.

Taken together, it was confirmed that oral administration of BS012 to the DNCB-induced atopic dermatitis model results in inhibition of atopic-associated biomarkers and reduction of the levels of epidermal hyperplasia, mast cell infiltration, and inflammation due to atopic dermatitis. In particular, the BS012 administration at a dose of 100 mg/kg and 200 mg/kg showed an activity equal to or higher than that of dexamethasone (i.e., a strong steroid), suggesting that BS012 may be used as a natural drug candidate to replace the adrenal corticosteroid drug in the existing market of bronchial asthma control agents.

In the present specification, details which can be sufficiently recognized and inferred by one of ordinary skill in the technical field of the present invention are omitted. In addition to the specific examples described in the present specification, more various modifications may be made without changing the technical spirit or essential configuration of the present invention. Accordingly, the present invention may be implemented in a manner different from those specifically described and illustrated in the present specification, which is a matter that can be understood by one of ordinary skill in the technical field of the present invention.

The invention claimed is:

1. A method for preventing or treating an allergic disease comprising: administering a composition consisting of a mixed extract of *Asiasarum* root, *Platycodon* root, and *Cinnamomi* ramulus to a subject.

2. The method of claim 1, wherein the mixed extract is an extract obtained using any one solvent selected from water, C1 to C4 alcohol, and a mixture thereof.

3. The method of claim 2, wherein the solvent is ethanol.

4. The method of claim 1, wherein the allergic disease is an allergic respiratory disease or atopic dermatitis.

5. The method of claim 4, wherein the allergic respiratory disease is bronchitis, bronchial asthma, or allergic rhinitis.

6. The method of claim 1, wherein the prevention or treatment an allergic disease is achieved by inhibition of Th2 cell differentiation.

* * * * *